(12) United States Patent
Yamada et al.

(10) Patent No.: US 8,258,243 B2
(45) Date of Patent: Sep. 4, 2012

(54) GRAFTED SILICONE POLYMER AND PRODUCTS MADE THEREWITH

(75) Inventors: Takeshi Yamada, Tokyo (JP); Satoshi Haramizu, Tokyo (JP)

(73) Assignee: 3M Innovative Properties Company, Saint Paul, MN (US)

( * ) Notice: Subject to any disclaimer, the term of this patent is extended or adjusted under 35 U.S.C. 154(b) by 339 days.

(21) Appl. No.: 12/596,859

(22) PCT Filed: Apr. 24, 2008

(86) PCT No.: PCT/US2008/061421
§ 371 (c)(1),
(2), (4) Date: Oct. 21, 2009

(87) PCT Pub. No.: WO2008/134428
PCT Pub. Date: Nov. 6, 2008

(65) Prior Publication Data
US 2010/0130693 A1    May 27, 2010

(30) Foreign Application Priority Data
Apr. 27, 2007  (JP) ................. 2007-119340

(51) Int. Cl.
*C08F 283/12* (2006.01)
*C08G 77/28* (2006.01)
*C08G 77/38* (2006.01)
*C08G 77/442* (2006.01)
(52) U.S. Cl. ............ 525/479; 528/32; D28/4; 525/326.5
(58) Field of Classification Search ............ 525/479
See application file for complete search history.

(56) References Cited

U.S. PATENT DOCUMENTS

| | | | | | |
|---|---|---|---|---|---|
| 3,575,910 | A | * | 4/1971 | Thomas | 524/588 |
| 4,071,577 | A | * | 1/1978 | Falender et al. | 525/479 |
| RE30,431 | E | * | 11/1980 | Falender et al. | 525/479 |
| 4,985,155 | A | | 1/1991 | Yamada et al. | |
| 4,987,180 | A | * | 1/1991 | Ohata et al. | 524/860 |
| 5,032,460 | A | | 7/1991 | Kantner et al. | |
| 5,061,481 | A | | 10/1991 | Suzuki et al. | |
| 5,079,298 | A | * | 1/1992 | Kuriyama et al. | 525/100 |

(Continued)

FOREIGN PATENT DOCUMENTS
EP      0421588 A    4/1991
(Continued)

OTHER PUBLICATIONS

Fedors, Robert J., "A Method for Estimating Both the Solubility Parameters and Molar Volumes of Liquids", Polymer Engineering and Science, (Jun. 1974), p. 147, vol. 14.

(Continued)

*Primary Examiner* — Randy Gulakowski
*Assistant Examiner* — Mike M Dollinger
(74) *Attorney, Agent, or Firm* — Lynn R. Hunsberger

(57) ABSTRACT

The grafted silicone polymer comprises a polymerization product of (a) a mercapto-modified silicone polymer and (b) a radically polymerizable monomer component comprising (meth)acrylic acid and/or a (meth)acrylic acid alkyl ester selected so that the solubility parameter of a polymer obtained only from the radically polymerizable monomer component is at least 9.14 $(cal/cm^3)^{1/2}$, wherein the grafted silicone polymer has a elastic storage modulus of 1 Œ 105 Pa or greater at 37° C., 1 Hz and dissolves in decamethylcyclopentasiloxane by 1 weight percent or greater at 23° C.

8 Claims, 7 Drawing Sheets

U.S. PATENT DOCUMENTS

| | | | |
|---|---|---|---|
| 5,079,313 A | 1/1992 | Okuno et al. | |
| 5,232,997 A * | 8/1993 | Itoh et al. | 525/477 |
| 5,234,736 A * | 8/1993 | Lee | 428/41.5 |
| 5,274,053 A * | 12/1993 | Kurata et al. | 525/479 |
| 5,278,228 A * | 1/1994 | Matner et al. | 524/837 |
| 5,468,477 A * | 11/1995 | Kumar et al. | 424/78.17 |
| 5,635,331 A * | 6/1997 | Kangas et al. | 430/260 |
| 5,725,882 A * | 3/1998 | Kumar et al. | 424/486 |
| 5,744,207 A * | 4/1998 | Bartusiak et al. | 428/41.8 |
| 6,506,376 B2 | 1/2003 | Sato | |
| 7,886,499 B2 * | 2/2011 | Okuda et al. | 52/750 |
| 2004/0081764 A1 | 4/2004 | Liu et al. | |
| 2004/0147189 A1 * | 7/2004 | Smith et al. | 442/121 |
| 2007/0258923 A1 * | 11/2007 | Bui et al. | 424/63 |
| 2007/0258933 A1 * | 11/2007 | Bui et al. | 424/70.11 |
| 2010/0130693 A1 | 5/2010 | Yamada et al. | |

FOREIGN PATENT DOCUMENTS

| | | |
|---|---|---|
| EP | 1044673 A | 10/2000 |
| JP | 45-2915 | 1/1970 |
| JP | 61065808 A | 4/1986 |
| JP | 6116121 A | 7/1986 |
| JP | 3086775 A | 4/1991 |
| JP | 04-018009 | 1/1992 |
| JP | 05-339125 | 12/1993 |
| JP | 6092825 A | 4/1994 |
| JP | 6271427 A | 9/1994 |
| JP | 6271436 A | 9/1994 |
| JP | 07-196946 | 8/1995 |
| JP | 7508027 W | 9/1995 |
| JP | 2539190 B2 | 10/1996 |
| JP | 2700816 B2 | 1/1998 |
| JP | 2799219 B2 | 9/1998 |
| JP | 10512233 W | 11/1998 |
| JP | 11-035831 | 2/1999 |
| JP | 2939309 B2 | 8/1999 |
| JP | 2001 151642 | 6/2001 |
| JP | 2002 255731 A | 9/2002 |
| JP | 3552741 B2 | 8/2004 |
| JP | 2007119340 | 5/2007 |
| WO | WO 9323009 A | 11/1993 |
| WO | WO 9503776 A | 2/1995 |

OTHER PUBLICATIONS

International Search Report from International Application No. PCT/US2008/061421 Filed on Apr. 24, 2008.

\* cited by examiner

GRAFTED SILICONE POLYMER AND PRODUCTS MADE THEREWITH

CROSS REFERENCE TO RELATED APPLICATIONS

This application is a national stage filing under 35 U.S.C. 371 of PCT/US2008/061421, filed Apr. 24, 2008, which claims priority to Japanese Application No. 2007-119340, filed Apr. 27, 2007, the disclosure of which is incorporated by reference in its/their entirety herein.

BACKGROUND OF THE INVENTION

1. Field of the Invention

The present invention relates to grafted silicone polymers and to products made therewith, especially personal care products including cosmetics.

2. Related Background Art

Cosmetics are widely used for cleaning, care, protection and appearance enhancement of skin, hair and nails. Skin cosmetics prepared in the forms of gels, emulsions or creams are used for prevention and amelioration of rough skin that may result when skin is washed or exposed to water in the workplace. Such skin cosmetics adjust the skin moisture balance by supplying water, moisturizing agents and oils to the skin, thus having a moistening and softening effect.

Housewives, physicians and barbers are among those that perform cleaning or otherwise work with water and are at risk of suffering from roughened skin. Skin roughening may progress before moisture, moisturizing agents and oils can be supplied, often producing inflammation in more serious cases. When this occurs, it is the usual practice to apply a hand cream that includes petrolatum or a moisturizing agent as non-volatile components. However, since hand creams wash away during cleaning or working with water and tend to stick to objects that are contacted, they may require frequent re-application to maintain the therapeutic benefits and usually do not have long-term durability.

Skin-protecting cosmetics that form water-resistant coatings on the skin prior to some user activity are useful by helping avoids loss of moisture, natural moisturizing factors and lipids experienced during subsequent cleaning or working with water, thus helping to prevent skin roughening. Such cosmetics usually contain silicone oils or film-forming acrylic polymers or silicone polymers to provide water repellency.

Skin-protecting cosmetics employing organic silicone resins are disclosed, for example, in Japanese Examined Patent Publication No. 6-15448 and Japanese Patent Publication No. 2539190.

Other skin-protecting cosmetics include sunscreen cosmetics that protect skin by blocking ultraviolet ray components in sunlight, namely UVA (320 nm-400 nm) and UVB (290 nm-320 nm), and suntan lotions that help produce uniformly tanned skin without causing UVB-induced erythema. Especially when used under the strong ultraviolet rays of summer, it is important for sunscreen cosmetics to form water-resistant coatings in order to fix the ingredients so that they do not escape into seawater or through sweat. Sunscreen cosmetics employing an organic silicone resin are disclosed, for example, in Japanese Examined Patent Publication No. 6-72085.

Hair care products utilize conditioning agents that include cationic surfactants or amino-modified silicones, but these can produce a sticky feel as well as allergic reactions. Although proteins are sometimes used as conditioning agents, their adhesion is poor and they are readily washed off by water.

Makeup cosmetics that are applied onto skin, hair and nails, and especially the skin and eyelashes, should form water-resistant and sebum-resistant coatings to prevent makeup deterioration or wear off due to sweat, tears and sebum. Improving the adhesion of makeup cosmetics to skin by dispersing pigments or inorganic powders in oil bases has been attempted, but this tends to produce a sticky feel. Japanese Patent Publication No. 3552741 discloses an eye makeup cosmetic that contains an organic silicone resin and an acrylic-silicone polymer obtained by radical polymerization of a radically polymerizable monomer composed mainly of a (meth)acrylic acid ester, with a dimethylpolysiloxane compound having a radically polymerizable group at one end of the molecular chain.

Japanese Patent Publication No. 2700816 also discloses application of an acrylic-silicone polymer, likewise obtained by radical polymerization of a radically polymerizable monomer (composed mainly of a (meth)acrylic acid ester with a dimethylpolysiloxane compound having a radically polymerizable group at one end of the molecular chain), for cosmetics. The basic structure of these polymers is composed of a silicone compound side chain grafted onto an acrylic polymer main chain.

Japanese Patent Publication No. 2939309 discloses a process for production of a vinyl-silicone polymer obtained by solution polymerization of a mercapto-modified silicone and a radically polymerizable vinyl monomer, as a film-forming agent with asserted superior adhesion and long-lasting functionability, as well as its application as a release coating for pressure-sensitive adhesives. This type of polymer has a structure with vinyl side chains grafted onto the silicone polymer main chain. The mercapto-modified silicone polymer is used as a chain transfer agent, and its reactivity is high. Because mercapto-modified silicone polymers can be prepared by several methods and their compositional ratios and molecular weights can be easily altered, a large variety of mercapto-modified silicone polymers are readily available. Japanese Laid-Open Patent Application No. 7-508027 and Japanese Laid-Open Patent Application No. 10-512233 disclose cosmetics employing vinyl-silicone polymers obtained by solution polymerization of mercapto-modified silicones with radically polymerizable vinyl monomers.

There has long been a need for 1) a polymer which has sufficiently high solubility in non-skin-irritating volatile solvents to thus ensure sufficient freedom of formulation, and which when used as a cosmetic component is able to form coatings with a minimal sticky feel on the skin coupled with satisfactory water and sebum resistance, and 2) cosmetics containing such polymers.

SUMMARY OF THE INVENTION

The present invention relates to a grafted silicone polymer comprising a polymerization product of (a) a mercapto-modified silicone polymer represented by general formula (1) below, and

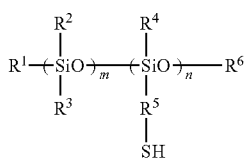

(1)

(b) a radically polymerizable monomer component comprising (meth)acrylic acid and/or a (meth)acrylic acid alkyl ester, selected so that the solubility parameter of a polymer obtained only from the radically polymerizable monomer component is at least 9.14 $(cal/cm^3)^{1/2}$, wherein the grafted silicone polymer has an elastic storage modulus of $1 \times 10^5$ Pa or greater at 37° C., 1 Hz and dissolves in decamethylcyclopentasiloxane in an amount of 1 weight percent or greater at 23° C.

In formula (1), R1, R2, R3, R4 and R6 each independently represent hydrogen, hydroxyl, allyl, C1-3 alkyl or a C1-3 halogenated alkyl group; R5 represents arylene or C1-3 alkylene, m represents an integer of 10-540 and n represents an integer of 1 or greater.

Here, the weight percentage (weight percent) is calculated according to the equation of [grafted silicone polymer weight]/[(grafted silicone polymer weight)+(decamethylcyclopentasiloxane weight)]. Also, the term "dissolve(s)" means a condition where polymer precipitation or solution opacity does not occur.

The grafted silicone polymer of the invention typically has a structure wherein side chains derived from component (b) are grafted onto the silicone polymer (component (a)) main chain, and shows the unique features of a solubility parameter, elastic storage modulus and/or solvent solubility as noted above. Therefore, the grafted silicone polymer of the invention exhibits high solubility in non-skin-irritating volatile solvents, and cosmetics prepared using the grafted silicone polymer form coatings with a minimal sticky feel on the skin and sufficiently high sebum resistance. In addition, a coated film of the cosmetics shows high water resistance to block sweat from the skin or water from the environment.

In a grafted silicone polymer of the invention, component (a) is preferably a mercapto-modified silicone polymer represented by the following general formula (2). In formula (2), m represents an integer of 10-540 and n represents an integer of 1 or greater.

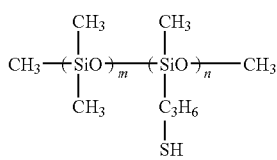

(2)

This grafted silicone polymer has high solubility in non-skin-irritating volatile solvents. In addition, the freedom of formulation for cosmetics is increased while the reduction in skin stickiness and the increase in water/sebum resistance are both satisfactory.

This invention also provides cosmetics containing the grafted silicone polymer described above. Such cosmetics containing the grafted silicone polymer exhibit lowered sticky feeling on skin and have a satisfactory degree of water and sebum resistance, making them particularly useful as cosmetics for external application on the skin.

DESCRIPTION OF THE PREFERRED EMBODIMENTS

Figure 1:
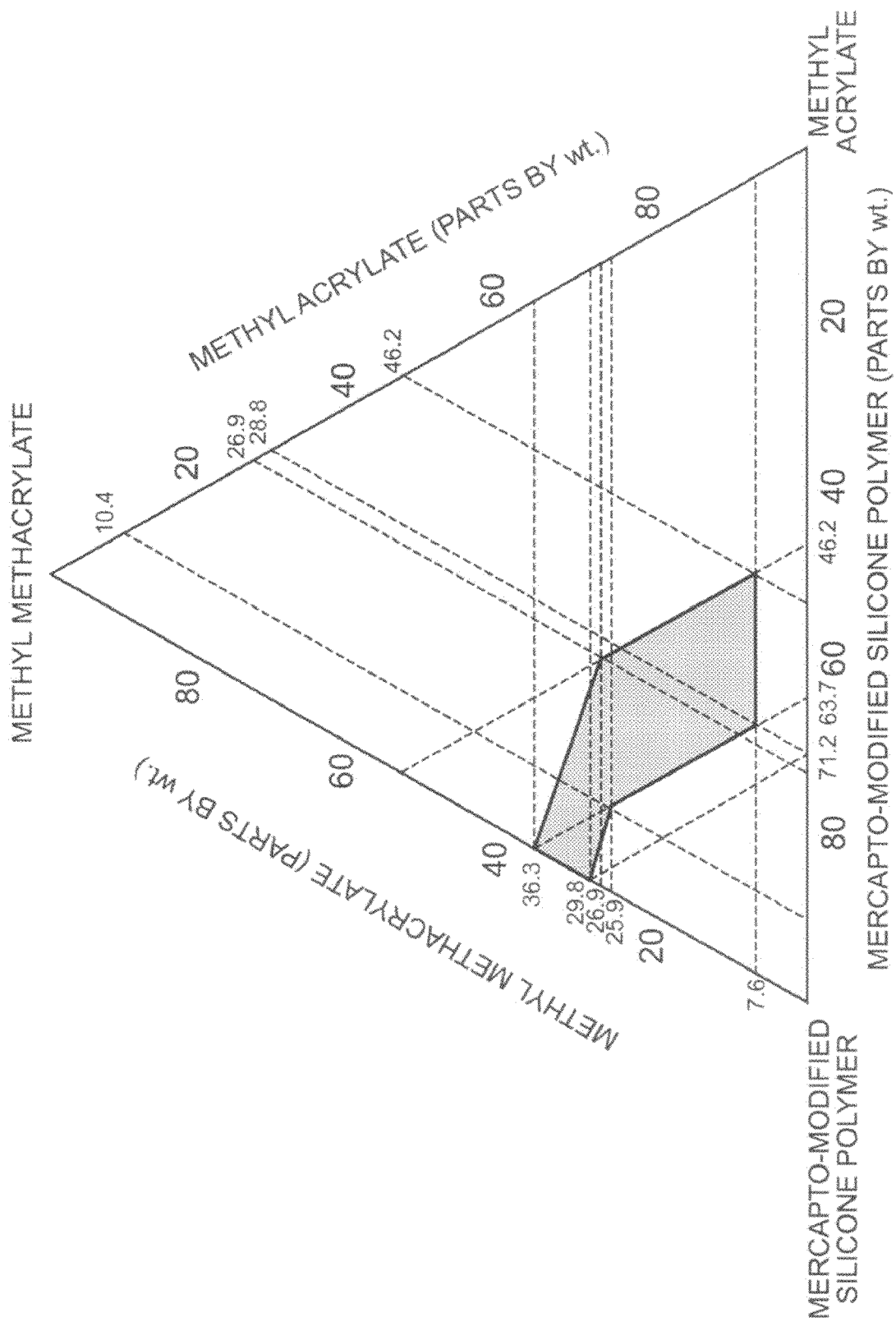
FIG. 1 is a ternary phase diagram for polymerization of the mercapto-modified silicone polymer (MMSP) represented by general formula (2), methyl methacrylate (MMA) and methyl acrylate (MA).

Preferred embodiments of the invention will now be explained in detail, with reference to the accompanying drawings as necessary. According to the invention, the term "(meth)acrylic acid" means acrylic acid or the corresponding methacrylic acid, while "(meth)acrylic acid alkyl ester" means "acrylic acid alkyl ester" or its corresponding "alkyl methacrylate ester".

The grafted silicone polymers of the invention can be obtained by polymerizing (a) a mercapto-modified silicone polymer with (b) a radically polymerizable monomer component comprising (meth)acrylic acid and/or a (meth)acrylic acid alkyl ester.

The mercapto-modified silicone polymer (component (a)) used for the invention is a compound represented by the following general formula (1).

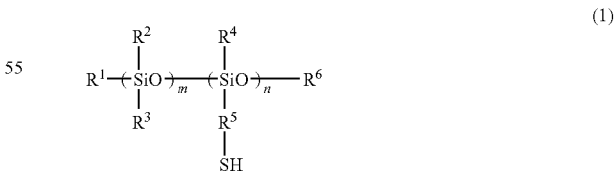

(1)

In this formula (1), R1, R2, R3, R4 and R6 each independently represent hydrogen, hydroxyl, allyl, C1-3 alkyl or a C1-3 halogenated alkyl group, and preferably R1, R2, R3, R4 and R6 each independently represent hydroxyl, ally, or C1-3 alkyl, more preferably C1-3 alkyl and most preferably methyl. R5 is an arylene or C1-3 alkylene. R5 is preferably C1-3 alkylene and more preferably propylene.

The mercapto-modified silicone polymer represented by general formula (1) is most preferably a compound represented by the following general formula (2).

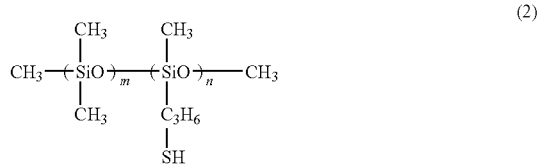

In the formulae (1) and (2), m is an integer of 10-540 and n is an integer of 1 or greater. When m becomes smaller, a sticky feeling on the skin will tend to be experienced. When m becomes bigger, the solubility in decamethylcyclopentasiloxane (DMCPS or D5) will tend to be reduced. Thus, m is preferably an integer in the range of 50-300. When n becomes smaller, the number of grafting of component (b) onto the mercapto-modified silicone polymer becomes less. When n becomes bigger, gelling will tend to occur during polymerization. Thus, n is preferably an integer of 1-50, more preferably an integer of 10-30.

The mercapto-modified silicone polymer as described above can be prepared by any desired process which is known, such as (1) co-hydrolysis of a mixture containing an organoalkoxysilane with one or more mercapto-substituted hydrocarbon groups and an organoalkoxysilane with no mercapto groups, (2) reaction of an organoalkoxysilane having one or more mercapto-substituted hydrocarbon groups with a cyclic organopolysiloxane or with a silanol-terminal diorganopolysiloxane with no mercapto groups, (3) equilibrium reaction between a cyclic or straight-chain organopolysiloxane with one or more mercapto-substituted hydrocarbon groups and a cyclic or straight-chain organopolysiloxane with no mercapto groups, (4) reaction between one or more nucleophilic groups and an electrophilic reagent to obtain a mercapto-modified silicone polymer, and (5) reaction between one or more electrophilic groups and a nucleophilic reagent to obtain a mercapto-modified silicone polymer.

The mercapto-modified silicone polymer represented by general formula (2) above is commercially available. Examples of such products include KF-2001 and KF-2004 by Shin-Etsu Chemical Co., Ltd., SMS-022, SMS-042 and SMS-992 by Gelest Inc. and PS848, PS849, PS849.5, PS850, PS850.5 and PS927 by United Chemical Corp. These products have different weight-average molecular weights, molecular weight distributions and mercapto group introduction rates, and may be selected for the invention according to preference.

The weight-average molecular weight of the mercapto-modified silicone polymer used as component (a) is preferably 750-40,000 and more preferably 3500-25,000. A weight-average molecular weight of less than 750 will tend to increase the feeling of stickiness on the skin, whereas at greater than 40,000, the solubility in DMCPS will tend to be poor.

The radically polymerizable monomer component (component (b)) used for the invention comprises (meth)acrylic acid and/or a (meth)acrylic acid alkyl ester. (Meth)acrylic acid and/or a (meth)acrylic acid alkyl ester used as component (b) may be, for example, methyl (meth)acrylate, ethyl (meth)acrylate, butyl (meth)acrylate, tert-butyl (meth)acrylate, isobutyl (meth)acrylate, 2-ethylhexyl (meth)acrylate, cetyl (meth)acrylate, stearyl (meth)acrylate or biphenyl (meth)acrylate. Component (b) may further comprise a radically polymerizable monomer other than (meth)acrylic acid or (meth)acrylic acid alkyl ester, and such monomer includes ethylene, propylene, styrene, vinyl acetate, vinyl ether, vinyl chloride, acrylonitrile, N-vinylpyrrolidone, butadiene, isoprene, and their derivatives. The proportion of (meth)acrylic acid and/or a (meth)acrylic acid alkyl ester in component (b) is preferably 50-100 weight percent, more preferably 80-100 weight percent and even more preferably 100 weight percent.

The grafted silicone polymer of the invention may be obtained by polymerizing the mercapto-modified silicone polymer described above with the radically polymerizable monomer component also described above, in the presence of a radical polymerization initiator. There is no limitation for suitable radical polymerization initiators. Specifically, azo compounds, peroxides, hydroxyperoxides, peracids and peresters may be used as thermopolymerization initiators. Examples of azo compounds include 2,2'-azobis-isobutyronitrile, 2,2'-azobis(2-methylbutyronitrile), dimethyl 2,2'-azobis-isobutyrate, dimethyl 2,2'-azobis(2-methylpropionate), azobis-diphenylmethane and 4,4'-azobis-(4-cyanopentanonoic acid). Examples of peroxides include benzoyl peroxide, cumyl peroxide, tert-butyl peroxide, cyclohexanone peroxide, glutaric peroxide, lauroyl peroxide, methyl ethyl ketone peroxide and hydrogen peroxide. Examples of hydroxyperoxides include tert-butyl hydroperoxide and cumene hydroperoxide. Examples of peracids include peracetic acid, perbenzoic acid and potassium persulfate. An example of a perester is diisopropyl percarbonate. Examples of photopolymerization initiators that may be used include benzoin ethers, diethoxyacetophenone, oxyiminoketone, acylphosphone oxide, diarylketone, benzophenone, 2-isopropylthioxanthone, benzyl, quinone derivatives and 3-ketocoumarin. Any of these compounds may be used alone, or two or more thereof may be used in combination.

The grafted silicone polymer of the invention is preferably produced by solution polymerization carried out in a solvent. The solvent used for the solution polymerization must be one that is inactive with respect to the monomers and the reaction product of the radical polymerization, and any organic solvent that does not inhibit the reaction is suitable. The solvent is also preferably a liquid at temperatures ranging from −10° C. to 50° C. More specifically, it is preferred to use an ester-based solvent, ketone-based solvent or alcohol-based solvent. As specific examples of these types of solvents there may be mentioned ethyl acetate and butyl acetate as ester-based solvents, acetone, methyl ethyl ketone, methyl isobutyl ketone and methyl propyl ketone as ketone-based solvents, and methanol, ethanol, isopropanol and butanol as alcohol-based solvents.

The grafted silicone polymer of the invention can be obtained by placing the mercapto-modified silicone polymer (component (a)), the radically polymerizable monomer component (component (b)), the radical polymerization initiator and the solvent in a vessel of choice, dissolving the radical polymerization initiator, and applying light or heat for radical polymerization. The resulting polymer can be recovered by solvent evaporation or precipitation in an appropriate solvent such as methanol, hexane or water. The grafted silicone polymer of this invention may also be in the form of a mixture of polymers with different polymerization degrees or polymer ends.

Polymer hardness and stickiness can, in most cases, be explained in terms of rheology. Generally speaking, polymers with high elastic storage modulus (G') values are hard, while those with low G' values are soft. A commonly known standard for describing polymer stickiness, or "tack" is the Dahlquist standard. According to the Dahlquist standard, measuring G' of a given pressure-sensitive adhesive at room temperature at a frequency of 1 Hz yields a value of below $3 \times 10^5$ Pa.

A high-tack polymer will produce a sticky feel for the user and is therefore undesirable as a film-forming polymer for formulation in cosmetics. However, a polymer with some degree of tack can provide a feeling of moistness rather than stickiness. Upon examining this phenomenon it was found that the "feel" can be explained on the basis of simply the G' value of the grafted silicone polymer, and this therefore differs from the Dahlquist standard for pressure-sensitive adhesives.

Specifically, if the G' value of a grafted silicone polymer is less than $1 \times 10^5$ Pa at 37° C., 1 Hz, the user may notice a sticky feel when the polymer is incorporated into a cosmetic, and for this reason it may be assumed that such a polymer is not suitable as a film-forming polymer for cosmetics.

The grafted silicone polymer of the invention must therefore have a G' value of $1 \times 10^5$ Pa or greater as measured at 37° C., 1 Hz. If this standard is met it should be possible to formulate the grafted silicone polymer of the invention into cosmetics and predict the feel of the cosmetic without actual human testing. That is to say, cosmetics containing grafted silicone polymers with G' values of less than $1 \times 10^5$ Pa are undesirable because they typically produce a sticky feel. However, as long as the G' value is $1 \times 10^5$ Pa or greater, a relative comparison shows that grafted silicone polymers with lower G' values produce moist feels while those with even higher G' values produce smooth silky feels. In other words, the optimum grafted silicone polymer for the feel desired for the cosmetic may be selected without actual testing of the cosmetic. This G' value can be measured with a parallel disk-type rotating rheometer.

The G' value of the grafted silicone polymer may be adjusted by the weight-average molecular weight of the mercapto-modified dimethylpolysiloxane (component (a)) used, the type of radically polymerizable monomer component (component (b)), the mixing proportions of each of the starting materials, the conditions for polymerization, and other factors. If a high G' value is desired, this can be achieved by, for example, increasing the weight-average molecular weight of the mercapto-modified dimethylpolysiloxane, using a radically polymerizable monomer component that gives a high glass transition temperature polymer, increasing the mixing proportion of the radically polymerizable monomer component, reducing the concentration of the radical polymerization initiator, and/or lowering the polymerization temperature. On the other hand if a low G' value is desired, this can be achieved by reducing the weight-average molecular weight of the mercapto-modified dimethylpolysiloxane, using a radically polymerizable monomer component that gives a low glass transition temperature polymer, lowering the mixing proportion of the radically polymerizable monomer component, increasing the concentration of the radical polymerization initiator, and/or raising the polymerization temperature. There is no particular upper limit set for the G' value, but a value of no greater than $1 \times 10^9$ Pa may be preferred. The preferred range for the grafted silicone polymer G' value is $1.1 \times 10^5$-$4.1 \times 10^7$ Pa in order to ensure that the sticky feel is reduced.

Nevertheless, makeup on the skin may wear off easily for various reasons even when using a cosmetic containing a film-forming polymer with no sticky feel. For example, it may become sticky due to absorption of sweat, tears or sebum, or the coating may dissolve and cause makeup deterioration. The properties of polymer compatibility and solubility can be described by the solubility parameter (SP value).

Film-forming polymers with high sebum compatibility or solubility are prone to stickiness and makeup deterioration, and substances with similar SP values generally tend to be compatible or mutually soluble. However, no such correlation between SP value, based on the grafted silicone polymer composition ratio, and sebum resistance has been seen with the grafted silicone polymer of the invention. When this was examined in greater detail, it was found that sebum resistance is dependent not on the SP value of the grafted silicone polymer, but rather merely on the SP value of a polymer obtained by polymerizing the radically polymerizable monomer component (component (b)) alone. This phenomenon contrasts with the commonly held theory of compatibility or solubility based on SP value. Specifically, it has been found that if the SP value of the (meth)acrylic polymer (component (b)) in the grafted silicone polymer of the invention is at least $9.14 \, (cal/cm^3)^{1/2}$ [$1 \, (cal/cm^3)^{1/2}$=$2.046 \, (MPa)^{1/2}$], then stickiness due to sebum does not result.

The SP value can be calculated with reference to an article by Fedors published in Polymer and Engineering Science, 1974 (Fedors, R F: A method for estimating both the solubility parameters and molar volumes of liquids. Polymer and Engineering Science, 1974 14:147-154).

Using the SP value as the standard allows sebum resistance to be estimated before producing the grafted silicone polymer. It is thereby possible to know sebum resistance without actual production of cosmetics containing the grafted silicone polymer. An SP value of less than $9.14 \, (cal/cm^3)^{1/2}$ will result in reduced sebum resistance of the grafted silicone polymer, whereas an SP value of greater than $9.14 \, (cal/cm^3)^{1/2}$ will ensure that the grafted silicone polymer has high sebum resistance suitable for preparation of a long-term durability cosmetic. No upper limit need be specified for the SP value, but a preferred range is no higher than $12 \, (cal/cm^3)^{1/2}$. For more assuredly improved sebum resistance, the SP value is preferably $9.18$-$12 \, (cal/cm^3)^{1/2}$ and more preferably $9.18$-$10.23 \, (cal/cm^3)^{1/2}$.

The SP value of the side chains formed by polymerization of the radically polymerizable monomer component can be adjusted by the type and mixing proportions of the radically polymerizable monomer used as component (b). If it is desired to increase the SP value, for example, a monomer with an ionic group such as (meth)acrylic acid or a (meth)acrylic acid ester comprising (meth)acrylic acid and short alkyl groups may be used. Such monomers tend to give high glass transition temperatures when polymerized, and therefore grafted silicone polymers containing high proportions of the monomers have high G' values and produce a smooth, silky feel. If the goal is a grafted silicone polymer that produces a moist feel while maintaining sebum resistance, it is preferred to incorporate a (meth)acrylic acid alkyl ester comprising (meth)acrylic acid and long alkyl groups in order to achieve an SP value of $9.14 \, (cal/cm^3)^{1/2}$ or greater. Such monomers tend to give low glass transition temperatures when polymerized, and therefore grafted silicone polymers containing high proportions of these monomers have low G' values and produce a more moist feel.

The grafted silicone polymer of the invention may be combined with any desired materials commonly used in cosmetics to formulate a satisfactory cosmetic product. Materials used in cosmetics include hydrocarbons, fats and oils that are liquid at room temperature, fats and oils that are solids at room temperature, waxes, lower alcohols, higher alcohols, polyhydric alcohols, esters, silicone oils, fluorine-based solvents and the like. Specifically, the following compounds may be mentioned. As examples of hydrocarbons there may be mentioned liquid paraffin, isoparaffin, heavy liquid isoparaffin, paraffin, ozokerite, squalane, vegetable squalane, pristane, ceresin, squalene, petrolatum, microcrystalline wax, paraffin wax, montan wax, olefin oligomer, polyisobutylene, polybutene and hydrogenated polyisobutene. Examples of fats and oils that are liquid at room temperature include avocado oil, camellia oil, turtle oil, macadamia nut oil, corn oil, sunflower oil, mink oil, olive oil, rapeseed oil, egg yolk oil, sesame oil, persic oil, wheat germ oil, sasanqua oil, castor oil, linseed oil, safflower oil, grapeseed oil, cottonseed oil, perilla oil, soybean oil, peanut oil, tea seed oil, kaya oil, rice bran oil, China wood oil, tung oil, jojoba oil, germ oil and evening primrose oil. Examples of fats and oils that are solid at room temperature include cocoa butter, coconut oil, beef tallow, mutton tallow, horse fat, palm kernel oil, lard, beef bone fat, Japan wax oil, neat's-foot oil, Japan wax, hydrogenated coconut oil, hydrogenated palm oil, hydrogenated beef tallow, hydrogenated oil and hydrogenated castor oil. Examples of waxes include beeswax, candelilla wax, cotton wax, carnauba wax, bayberry wax, Chinese wax, whale wax, montan wax, rice bran wax, kapok wax, sugarcane wax, lanolin, lanolin acetate, liquid lanolin, isopropyl lanolate, reduced lanolin, hard lanolin, hexyl laurate, jojoba wax, shellac wax, POE lanolin alcohol ether, POE lanolin alcohol acetate, POE cholesterol ether, polyethylene glycol lanolate and POE hydrogenated lanolin alcohol ether. As examples of lower alcohols there may be mentioned ethanol and isopropanol. Examples of higher alcohols include straight-chain alcohols such as lauryl alcohol, cetyl alcohol, stearyl alcohol, behenyl alcohol, myristyl alcohol, oleyl alcohol and cetostearyl alcohol, and branched alcohols such as monostearylglycerin ether (batyl alcohol), 2-decyltetradecinol, lanolin alcohol, cholesterol, phytosterol, hexyldodecanol, isostearyl alcohol and octyldodecanol. Examples of polyhydric alcohols include propylene glycol, ethylene glycol, dipropylene glycol, diethylene glycol, 1,3-butyleneglycol, glycerin and the like. Examples of esters include isopropyl myristate, cetyl isooctanoate, octyldodecyl myristate, isopropyl palmitate, isooctyl palmitate, butyl stearate, hexyl laurate, myristyl myristate, decyl oleate, hexyldecyl dimethyloctanoate, cetyl lactate, myristyl lactate, octyldodecyl lactate, lanolin acetate, isocetyl stearate, isocetyl isostearate, cholesteryl 1,2-hydroxystearate, phytostearyl 1,2-hydroxystearate, phytostearyl oleate, ethyleneglycol di-2-ethylhexanoate, propyleneglycol dicaproate, dipentaerythritol fatty acid esters, N-alkylglycol monoisostearate, neopentylglycol dicaprate, diisostearyl malate, glycerin di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, glyceryl tri(caprylate/caprate), tri(caprylic/capric/myristic/stearic) glyceride, trimethylolpropane triisostearate, cetyl 2-ethyl hexanoate, 2-ethylhexyl palmitate, glycerin trimyristate, tri-2-heptylundecanoic glyceride, polyglyceryl diisostearate, polyglyceryl triisostearate, polyglyceryl tetraisostearate, diglyceryl triisostearate, diglyceryl tetraisostearate, erythrityl tri-2-ethylhexanoate, ditrimethylolpropane tri-2-ethylhexanoate, (isostearic/sebacic)ditrimethylolpropane oligoesters, castor oil fatty acid methyl esters, oleyl oleate, acetoglyceride, 2-heptylundecyl palmitate, diisobutyl adipate, (adipic/2-ethylhexanoic/stearic)glycerin oligoesters, (2-hexyldecanoic/sebacic)diglyceryl oligoesters, N-lauroyl-L-glutamic-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate and triethyl citrate. Examples of silicone oils include straight-chain silicone oils such as dimethylpolysiloxane, methylphenylpolysiloxane and methylhydrogenpolysiloxane, modified silicone oils such as polyoxyethylenepolyalkylsiloxane, and cyclic silicone oils such as octamethylcyclotetrasiloxane, decamethylcyclopentasiloxane (DMCPS), dodecamethylcyclohexasiloxane and tetrahydrotetramethylcyclotetrasiloxane. Examples of fluorine-based solvents include methylperfluorobutyl ether, methylperfluoroisobutyl ether, ethylperfluorobutyl ether and ethylperfluoroisobutyl ether.

The substance used for dissolution must be a volatile solvent if the grafted silicone polymer of the invention is to be formulated in a cosmetic and form a coating with excellent water and sebum resistance on the skin. However, dissolution in a volatile hydrocarbon such as hydrogenated polyisobutene may leave the undesirable odor of the hydrocarbon in the cosmetic. In addition, dissolution in volatile alcohols such as ethanol or isopropanol or volatile esters such as ethyl acetate can irritate the skin and leave characteristic odors in the cosmetics.

On the other hand, volatile silicone oils are widely used in cosmetics since they are odorless and relatively non-irritating to skin. The volatile silicone oil DMCPS is especially suitable as a volatile solvent for cosmetics, because it is not only odorless and relatively non-irritating to skin, but has a moderate evaporation rate allowing it to evaporate and dry rapidly after spreading of the cosmetic. Therefore, the grafted silicone polymer of the invention is also preferably used after dissolution in DMCPS.

When the grafted silicone polymer of the invention is poorly soluble in DMCPS, the viscosity increases during use and may adversely affect the sensation when using the cosmetic, or precipitation may occur with time and/or with changes in temperature. After experiments on the sensation during use and the stability of cosmetics, as well as the freedom of their formulation, it was found that excellent properties are exhibited when the solubility of the grafted silicone polymer of the invention in DMCPS at 23° C. is at least 1 weight percent (preferably at least 1.5 weight percent and more preferably at least 2 weight percent). The "solubility" referred to here is a state with no polymer precipitation or solution opacity. The solubility of the grafted silicone polymer of the invention in DMCPS is mainly affected by the mixing ratio of the mercapto-modified silicone polymer and the radically polymerizable monomer component, and by the type of radical polymerization initiator used. The solubility in DMCPS can be improved by increasing the amount of mercapto-modified silicone polymer added, reducing the amount of monomers with ionic groups such as (meth)acrylic acid, and using a (meth)acrylic acid ester with long alkyl groups.

Specifically, if the solubility parameter of a polymer obtained only from component (b) is 9.14 $(cal/cm^3)^{1/2}$ or greater and the grafted silicone polymer exhibits a elastic storage modulus of $1 \times 10^5$ Pa or greater at 37° C., 1 Hz and dissolves in DMCPS in an amount of 1% or greater at 23° C., it will be possible to lower stickiness of the skin, satisfactorily reduce irritation to skin and form a coating with excellent sebum resistance when the grafted silicone polymer is used in a cosmetic product. Solubility in DMCPS will permit greater freedom of cosmetic formulation and greater applicability.

Without being limited to any particular theory, it is merely conjectured that the sebum resistance is improved by restricting the solubility parameter to above value, and that stickiness is prevented by restricting the elastic storage modulus to above value. Preferred compositions for the grafted silicone polymer of the invention are listed below.

FIG. 1 is a ternary phase diagram for polymerization of the mercapto-modified silicone polymer (MMSP) represented by general formula (2), methyl methacrylate (MMA) and methyl acrylate (MA). According to the ternary phase diagram shown in FIG. 1, the grafted silicone polymer preferably has a composition in the range defined by:
(MMSP)/(MMA)/(MA)=63.7/36.3/0.0
(MMSP)/(MMA)/(MA)=46.2/26.9/26.9
(MMSP)/(MMA)/(MA)=46.2/7.6/46.2
(MMSP)/(MMA)/(MA)=63.7/7.6/28.7
(MMSP)/(MMA)/(MA)=63.7/25.9/10.4
(MMSP)/(MMA)/(MA)=71.2/29.8/0.0

Figure 2:
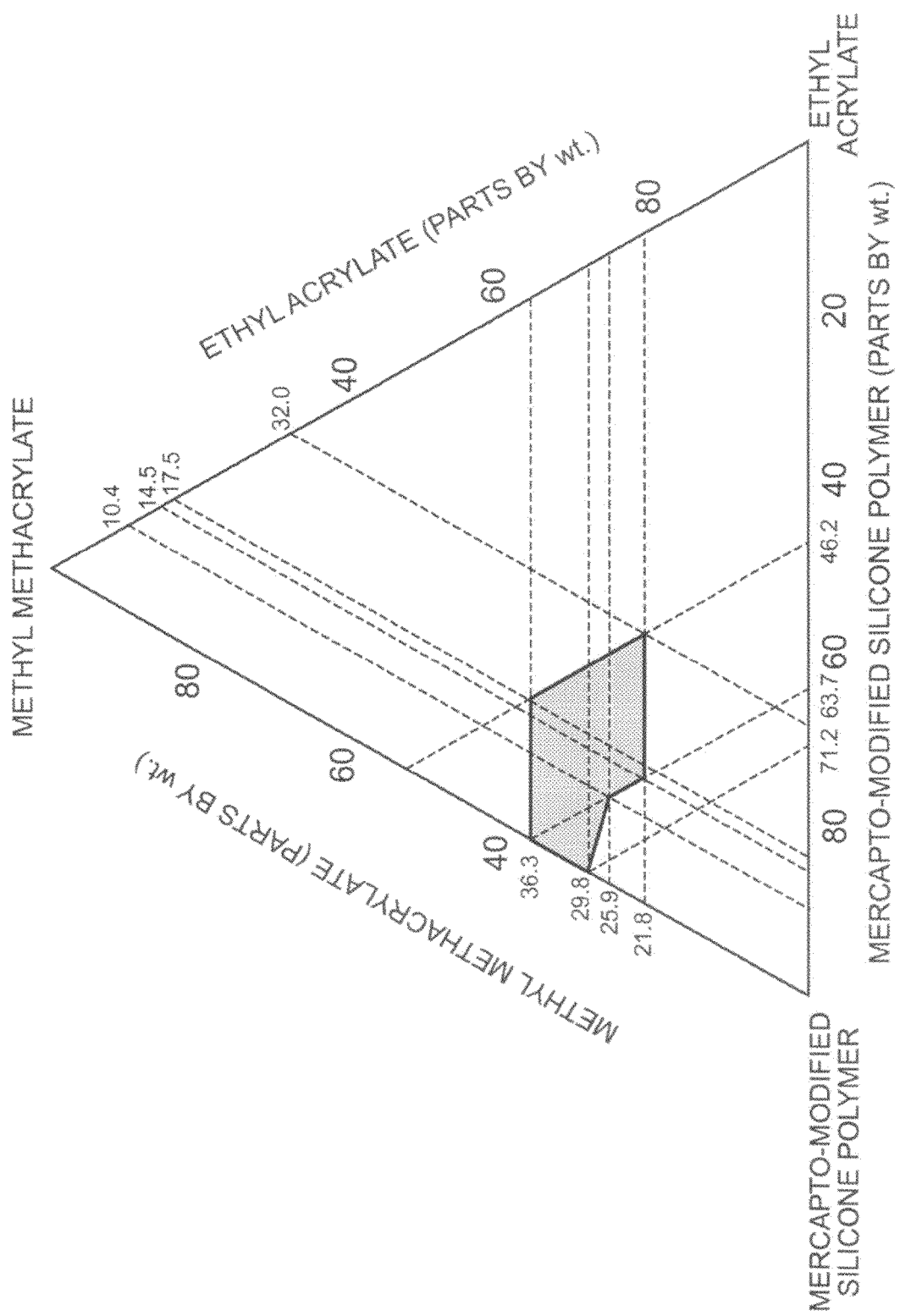
FIG. 2 is a ternary phase diagram for polymerization of the mercapto-modified silicone polymer (MMSP) represented by general formula (2), methyl methacrylate (MMA) and ethyl acrylate (EA).

FIG. 2 is a ternary phase diagram for polymerization of the mercapto-modified silicone polymer (MMSP) represented by general formula (2), methyl methacrylate (MMA) and ethyl acrylate (EA). According to the ternary phase diagram shown in FIG. 2, the grafted silicone polymer preferably has a composition in the range defined by:
(MMSP)/(MMA)/(EA)=63.7/36.3/0.0
(MMSP)/(MMA)/(EA)=46.2/36.3/17.5
(MMSP)/(MMA)/(EA)=46.2/21.8/32.0
(MMSP)/(MMA)/(EA)=63.7/21.8/14.5
(MMSP)/(MMA)/(EA)=63.7/25.9/10.4
(MMSP)/(MMA)/(EA)=71.2/29.8/0.0

Figure 3:
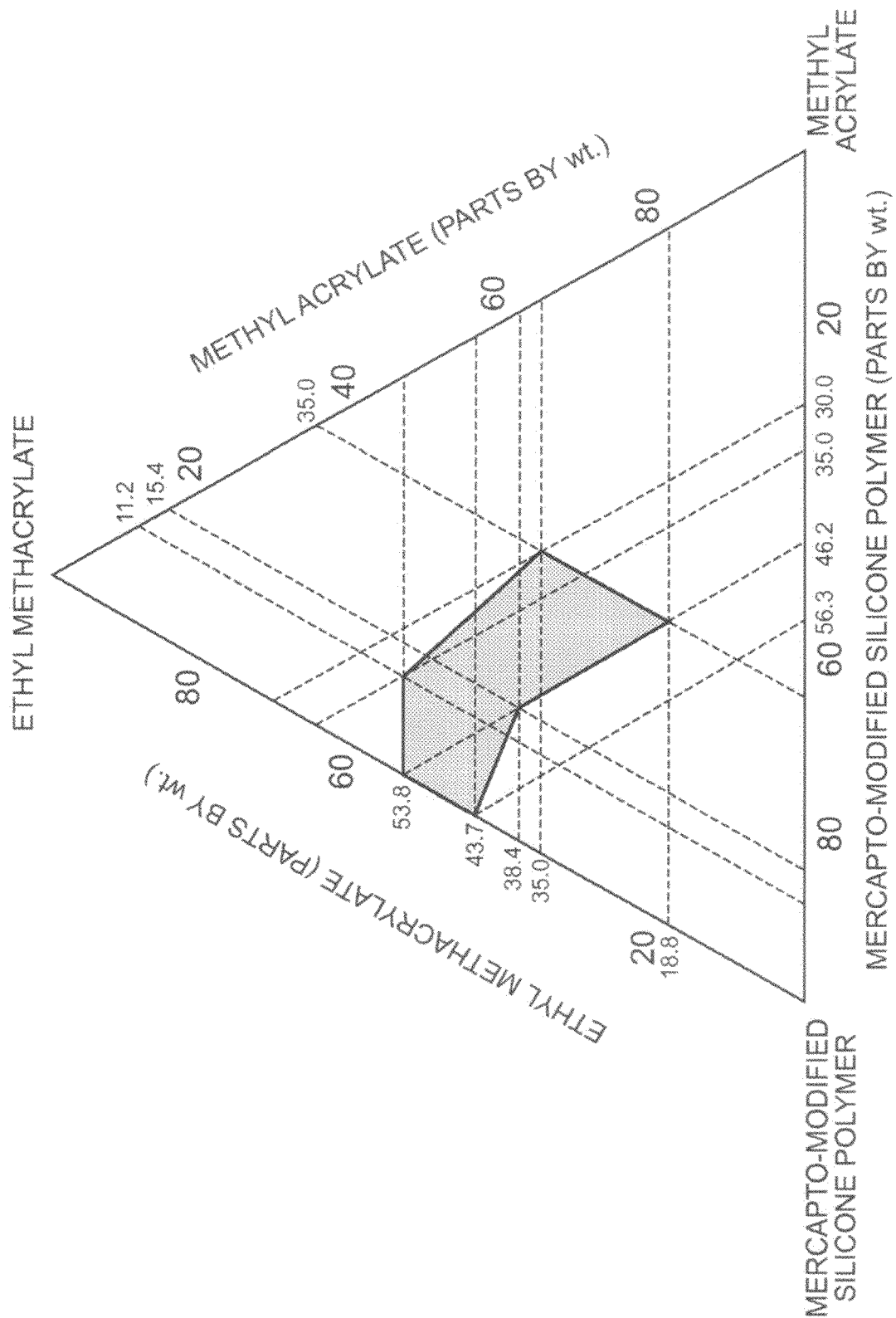
FIG. 3 is a ternary phase diagram for polymerization of the mercapto-modified silicone polymer (MMSP) represented by general formula (2), ethyl methacrylate (EMA) and methyl acrylate (MA).

FIG. 3 is a ternary phase diagram for polymerization of the mercapto-modified silicone polymer (MMSP) represented by general formula (2), ethyl methacrylate (EMA) and methyl acrylate (MA). According to the ternary phase diagram shown in FIG. 3, the grafted silicone polymer preferably has a composition in the range defined by:
(MMSP)/(EMA)/(MA)=46.2/53.8/0.0
(MMSP)/(EMA)/(MA)=35.0/53.8/11.2
(MMSP)/(EMA)/(MA)=30.0/35.0/35.0
(MMSP)/(EMA)/(MA)=46.2/18.8/35.0
(MMSP)/(EMA)/(MA)=46.2/38.4/15.4
(MMSP)/(EMA)/(MA)=56.3/43.7/0.0

Figure 4:
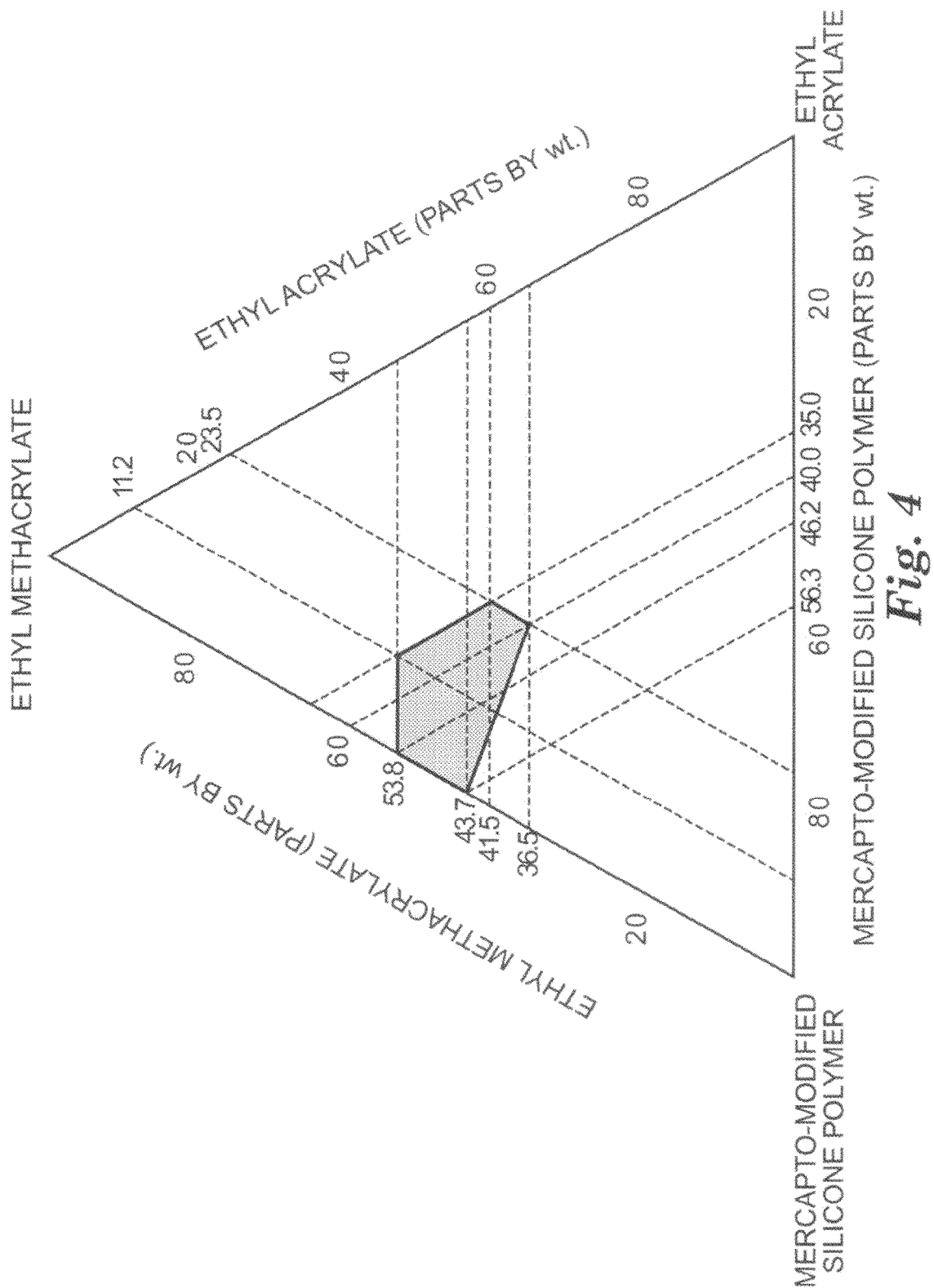
FIG. 4 is a ternary phase diagram for polymerization of the mercapto-modified silicone polymer (MMSP) represented by general formula (2), ethyl methacrylate (EMA) and ethyl acrylate (EA).

FIG. 4 is a ternary phase diagram for polymerization of the mercapto-modified silicone polymer (MMSP) represented by general formula (2), ethyl methacrylate (EMA) and ethyl acrylate (EA). According to the ternary phase diagram shown in FIG. 4, the grafted silicone polymer preferably has a composition in the range defined by:
(MMSP)/(EMA)/(EA)=46.2/53.8/0.0
(MMSP)/(EMA)/(EA)=35.0/53.8/11.2
(MMSP)/(EMA)/(EA)=35.0/41.5/23.5
(MMSP)/(EMA)/(EA)=40.0/36.5/23.5
(MMSP)/(EMA)/(EA)=56.3/43.7/0.0

Figure 5:
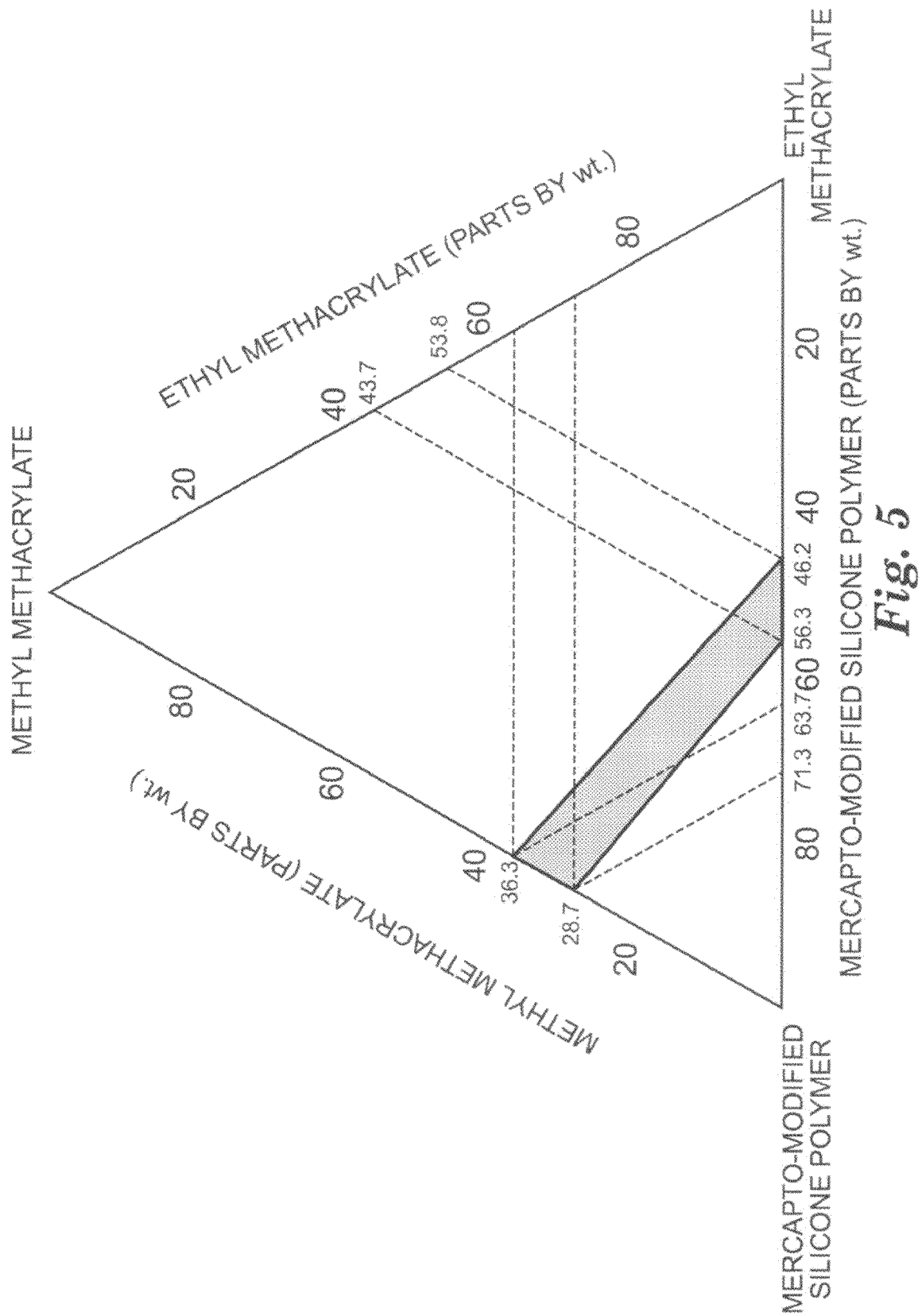
FIG. 5 is a ternary phase diagram for polymerization of the mercapto-modified silicone polymer (MMSP) represented by general formula (2), methyl methacrylate (MMA) and ethyl methacrylate (EMA).

FIG. 5 is a ternary phase diagram for polymerization of the mercapto-modified silicone polymer (MMSP) represented by general formula (2), methyl methacrylate (MMA) and ethyl methacrylate (EMA). According to the ternary phase diagram shown in FIG. 5, the grafted silicone polymer preferably has a composition in the range defined by:
(MMSP)/(MMA)/(EMA)=63.7/36.3/0.0
(MMSP)/(MMA)/(EMA)=46.2/0.0/53.8
(MMSP)/(MMA)/(EMA)=56.3/0.0/43.7
(MMSP)/(MMA)/(EMA)=71.3/28.7/0.0

Figure 6:
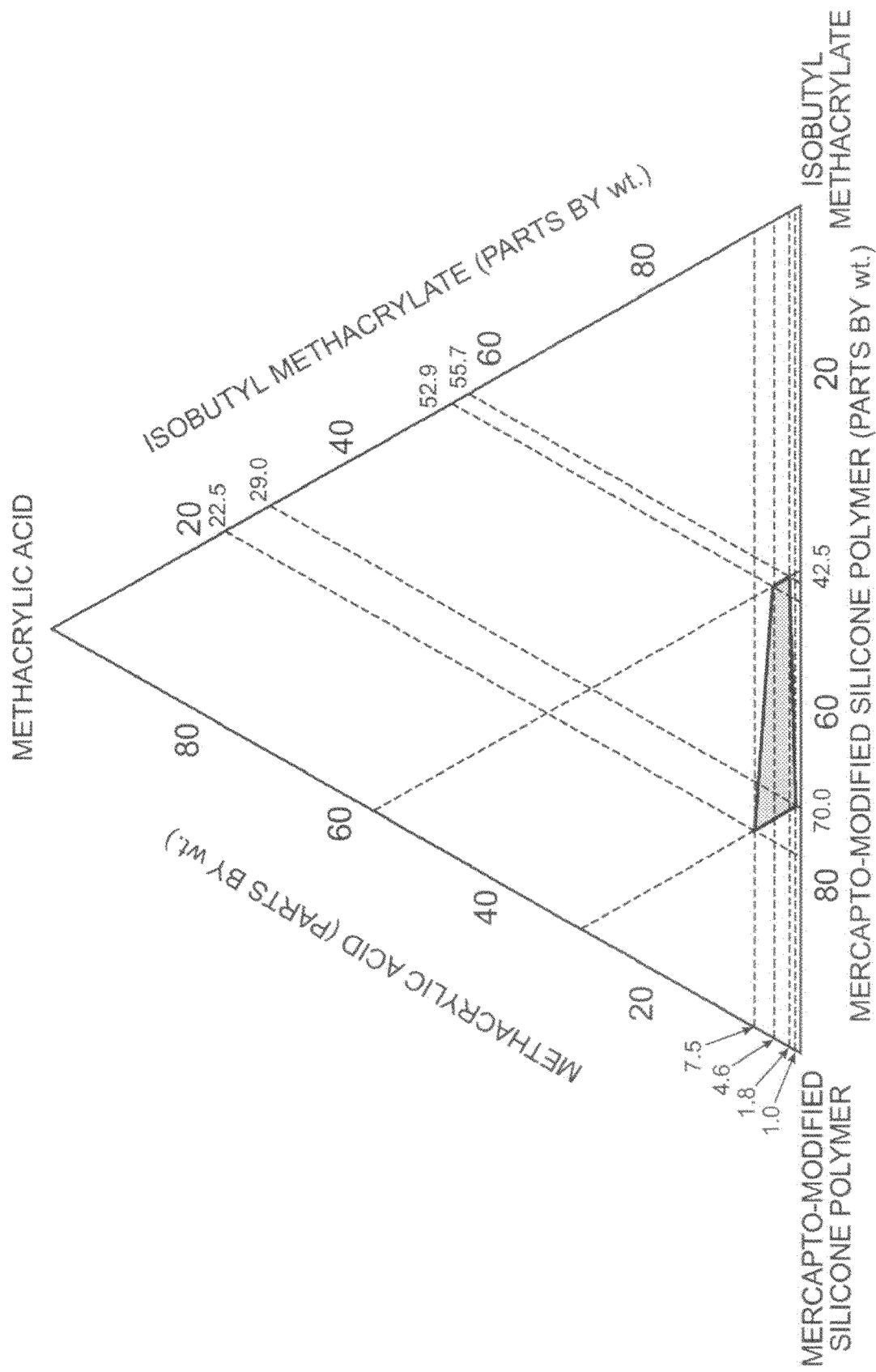
FIG. 6 is a ternary phase diagram for polymerization of the mercapto-modified silicone polymer (MMSP) represented by general formula (2), isobutyl methacrylate (IBMA) and methacrylic acid (MAA).

FIG. 6 is a ternary phase diagram for polymerization of the mercapto-modified silicone polymer (MMSP) represented by general formula (2), isobutyl methacrylate (IBMA) and methacrylic acid (MAA). According to the ternary phase diagram shown in FIG. 6, the grafted silicone polymer preferably has a composition in the range defined by:
(MMSP)/(IBMA)/(MAA)=70.0/22.5/7.5
(MMSP)/(IBMA)/(MAA)=42.5/52.9/4.6
(MMSP)/(IBMA)/(MAA)=42.5/55.7/1.8
(MMSP)/(IBMA)/(MAA)=70.0/29.0/1.0

When used in a cosmetic product, a grafted silicone polymer of the invention having a composition within these ranges produces low level of stickiness on the skin and can form a coating with excellent water and sebum resistance.

Cosmetics containing the grafted silicone polymer can be prepared into any of the forms, such as lotions, creams or solids, which are common for cosmetic products. When a grafted silicone polymer of the invention is dissolved in DMCPS, it can be used in combination with a DMCPS base, or as a water-in-oil (W/O) emulsion or oil-in-water (O/W) emulsion.

Such cosmetics have a wide variety of applications. For skin cosmetics, for example, they can be used as hand creams, sun-block creams, foundations, packs and the like. For make-up cosmetics, they can be used as powder refoundations, liquid foundations, lipsticks, lip glosses, eye liners, mascaras, eye shadows, eyebrow powder, nail enamels and the like. These types of cosmetics form flexible, smooth coatings on skin, hair or nails and exhibit excellent water resistance, sebum resistance, adhesion and sustained function.

The invention was explained in detail by the preferred embodiments, with the understanding that it is not limited thereto in any way. The invention may also be applied in a variety of other modes so long as the gist thereof is maintained.

EXAMPLES

The invention will now be explained in greater detail by the following examples, with the understanding that it is not limited thereto in any way.

Synthesis of Grafted Silicone Polymers

Example 1

After loading 67.5 parts by weight of mercapto-modified dimethylpolysiloxane ("KF-2001" by Shin-Etsu Chemical Co., Ltd., mercaptopropylmethylsiloxane units: 4 mol %, weight-average molecular weight: 20,000), 32.5 parts by weight of methyl methacrylate, 0.6 part by weight of dimethyl 2,2'-azobis(2-methylpropionate) and 102.4 parts by weight of methyl ethyl ketone (MEK) in a 225 mL glass bottle to a total of 162.4 g, the mixture was bubbled for 10 minutes with nitrogen gas. The vessel was then sealed and polymerization was conducted while stirring in a thermostatic bath at 65° C. After 24 hours, the vessel was removed from the thermostatic bath and cooled to room temperature. The polymerization solution was added dropwise to water while stirring, and the precipitate was recovered. The precipitate was dried at room temperature to obtain a grafted silicone polymer.

Example 2

In a 225 mL glass bottle there were loaded 60 parts by weight of the aforementioned mercapto-modified dimethylpolysiloxane "KF-2001", 28.56 parts by weight of methyl methacrylate, 11.44 parts by weight of methyl acrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Example 3

In a 225 mL glass bottle there were loaded 60 parts by weight of the aforementioned mercapto-modified dimethylpolysiloxane "KF-2001", 15 parts by weight of methyl methacrylate, 25 parts by weight of methyl acrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Example 4

In a 140 mL glass bottle there were loaded 60 parts by weight of the aforementioned mercapto-modified dimethylpolysiloxane "KF-2001", 28.56 parts by weight of methyl methacrylate, 11.44 parts by weight of ethyl acrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Example 5

In a 225 mL glass bottle there were loaded 52.5 parts by weight of the aforementioned mercapto-modified dimethylpolysiloxane "KF-2001", 47.5 parts by weight of ethyl methacrylate, 0.6 part by weight of dimethyl 2,2'-azobis(2-methylpropionate) and 102.4 parts by weight of MEK to a total of 162.4 g, and the procedure was carried out in the same manner as Example 1. The polymerization solution was added dropwise to water while stirring, and the precipitate was recovered and dried at room temperature to obtain a grafted silicone polymer.

Example 6

In a 140 mL glass bottle there were loaded 40 parts by weight of the aforementioned mercapto-modified dimethylpolysiloxane "KF-2001", 42.8 parts by weight of ethyl methacrylate, 17.2 parts by weight of methyl acrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Example 7

In a 140 mL glass bottle there were loaded 40 parts by weight of the aforementioned mercapto-modified dimethylpolysiloxane "KF-2001", 42.8 parts by weight of ethyl methacrylate, 17.2 parts by weight of ethyl acrylate, 0.6 part by weight of dimethyl 2,2'-azobis(2-methylpropionate) and 102.4 parts by weight of MEK to a total of 101.5 g, and the procedure was carried out in the same manner as Example 1. The polymerization solution was added dropwise to water while stirring, and the precipitate was recovered and dried at room temperature to obtain a grafted silicone polymer.

Example 8

In a 140 mL glass bottle there were loaded 60 parts by weight of the aforementioned mercapto-modified dimethylpolysiloxane "KF-2001", 20 parts by weight of methyl methacrylate, 20 parts by weight of ethyl methacrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Example 9

In a 225 mL glass bottle there were loaded 60 parts by weight of the aforementioned mercapto-modified dimethylpolysiloxane "KF-2001", 35 parts by weight of isobutyl methacrylate, 5 parts by weight of methacrylic acid, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Example 10

In a 225 mL glass bottle there were loaded 45 parts by weight of the aforementioned mercapto-modified dimethylpolysiloxane "KF-2001", 51.6 parts by weight of isobutyl methacrylate, 3.4 parts by weight of methacrylic acid, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Example 11

In a 140 mL glass bottle there were loaded 52.5 parts by weight of the aforementioned mercapto-modified dimethylpolysiloxane "KF-2001", 17.8 parts by weight of methyl methacrylate, 29.7 parts by weight of methyl acrylate, 0.6 part by weight of dimethyl 2,2'-azobis(2-methylpropionate) and 102.4 parts by weight of MEK to a total of 101.5 g, and the procedure was carried out in the same manner as Example 1. The polymerization solution was added dropwise to water while stirring, and the precipitate was recovered and dried at room temperature to obtain a grafted silicone polymer.

Example 12

In a 140 mL glass bottle there were loaded 52.5 parts by weight of the aforementioned mercapto-modified dimethylpolysiloxane "KF-2001", 33.92 parts by weight of methyl methacrylate, 13.58 parts by weight of ethyl acrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Example 13

In a 140 mL glass bottle there were loaded 40 parts by weight of the aforementioned mercapto-modified dimethylpolysiloxane "KF-2001", 30 parts by weight of ethyl methacrylate, 30 parts by weight of methyl acrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 1

In a 225 mL glass bottle there were loaded 60 parts by weight of the aforementioned mercapto-modified dimethylpolysiloxane "KF-2001", 40 parts by weight of methyl methacrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Comparative Example 2

In a 225 mL glass bottle there were loaded 52.5 parts by weight of the aforementioned mercapto-modified dimethylpolysiloxane "KF-2001", 33.92 parts by weight of methyl methacrylate, 13.58 parts by weight of methyl acrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Comparative Example 3

In a 225 mL glass bottle there were loaded 40 parts by weight of the aforementioned mercapto-modified dimethylpolysiloxane "KF-2001", 20 parts by weight of methyl methacrylate, 40 parts by weight of methyl acrylate, 0.6 part by weight of dimethyl 2,2'-azobis(2-methylpropionate) and 102.4 parts by weight of MEK to a total of 162.4 g, and the procedure was carried out in the same manner as Example 1. The polymerization solution was added dropwise to water while stirring, and the precipitate was recovered and dried at room temperature to obtain a grafted silicone polymer.

Comparative Example 4

In a 225 mL glass bottle there were loaded 40 parts by weight of the aforementioned mercapto-modified dimethylpolysiloxane "KF-2001", 40 parts by weight of methyl methacrylate, 20 parts by weight of ethyl acrylate, 0.6 part by weight of dimethyl 2,2'-azobis(2-methylpropionate) and 102.4 parts by weight of MEK to a total of 162.4 g, and the procedure was carried out in the same manner as Example 1. The polymerization solution was added dropwise to water while stirring, and the precipitate was recovered and dried at room temperature to obtain a grafted silicone polymer.

Comparative Example 5

In a 140 mL glass bottle there were loaded 40 parts by weight of the aforementioned mercapto-modified dimethylpolysiloxane "KF-2001", 60 parts by weight of ethyl methacrylate, 0.6 part by weight of dimethyl 2,2'-azobis(2-methylpropionate) and 102.4 parts by weight of MEK to a total of 101.5 g, and the procedure was carried out in the same manner as Example 1. The polymerization solution was added dropwise to water while stirring, and the precipitate was recovered and dried at room temperature to obtain a grafted silicone polymer.

Comparative Example 6

In a 140 mL glass bottle there were loaded 30 parts by weight of the aforementioned mercapto-modified dimethylpolysiloxane "KF-2001", 50 parts by weight of ethyl methacrylate, 20 parts by weight of methyl acrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 7

In a 140 mL glass bottle there were loaded 30 parts by weight of the aforementioned mercapto-modified dimethylpolysiloxane "KF-2001", 50 parts by weight of ethyl methacrylate, 20 parts by weight of ethyl acrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 8

In a 140 mL glass bottle there were loaded 52.5 parts by weight of the aforementioned mercapto-modified dimethylpolysiloxane "KF-2001", 23.75 parts by weight of methyl methacrylate, 23.75 parts by weight of ethyl methacrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 9

In a 225 mL glass bottle there were loaded 60 parts by weight of the aforementioned mercapto-modified dimethylpolysiloxane "KF-2001", 32.5 parts by weight of isobutyl methacrylate, 7.5 parts by weight of methacrylic acid, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Comparative Example 10

In a 225 mL glass bottle there were loaded 45 parts by weight of the aforementioned mercapto-modified dimethylpolysiloxane "KF-2001", 50 parts by weight of isobutyl methacrylate, 5 parts by weight of methacrylic acid, 0.6 part by weight of dimethyl 2,2'-azobis(2-methylpropionate) and 102.4 parts by weight of MEK to a total of 162.4 g, and the procedure was carried out in the same manner as Example 1. The polymerization solution was added dropwise to water while stirring, and the precipitate was recovered and dried at room temperature to obtain a grafted silicone polymer.

Comparative Example 11

In a 140 mL glass bottle there were loaded 40 parts by weight of the aforementioned mercapto-modified dimethylpolysiloxane "KF-2001", 57.5 parts by weight of isobutyl methacrylate, 2.5 parts by weight of methacrylic acid, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 12

In a 225 mL glass bottle there were loaded 40 parts by weight of the aforementioned mercapto-modified dimethylpolysiloxane "KF-2001", 20 parts by weight of ethyl methacrylate, 40 parts by weight of methyl acrylate, 0.6 part by weight of dimethyl 2,2'-azobis(2-methylpropionate) and 102.4 parts by weight of MEK to a total of 162.4 g, and the procedure was carried out in the same manner as Example 1. The polymerization solution was added dropwise to water while stirring, and the precipitate was recovered and dried at room temperature to obtain a grafted silicone polymer.

Comparative Example 13

In a 225 mL glass bottle there were loaded 20 parts by weight of the aforementioned mercapto-modified dimethylpolysiloxane "KF-2001", 40 parts by weight of ethyl methacrylate, 40 parts by weight of methyl acrylate, 0.6 part by weight of dimethyl 2,2'-azobis(2-methylpropionate) and 102.4 parts by weight of MEK to a total of 162.4 g, and the procedure was carried out in the same manner as Example 1. The polymerization solution was added dropwise to water while stirring, and the precipitate was recovered and dried at room temperature to obtain a grafted silicone polymer.

Comparative Example 14

In a 225 mL glass bottle there were loaded 40 parts by weight of the aforementioned mercapto-modified dimethylpolysiloxane "KF-2001", 60 parts by weight of isobutyl methacrylate, 0.6 part by weight of dimethyl 2,2'-azobis(2-methylpropionate) and 102.4 parts by weight of MEK to a total of 162.4 g, and the procedure was carried out in the same manner as Example 1. The polymerization solution was added dropwise to water while stirring, and the precipitate was recovered and dried at room temperature to obtain a grafted silicone polymer.

Comparative Example 15

In a 225 mL glass bottle there were loaded 30 parts by weight of the aforementioned mercapto-modified dimethylpolysiloxane "KF-2001", 70 parts by weight of isobutyl methacrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Comparative Example 16

In a 225 mL glass bottle there were loaded 15 parts by weight of the aforementioned mercapto-modified dimethylpolysiloxane "KF-2001", 85 parts by weight of isobutyl methacrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Comparative Example 17

In a 140 mL glass bottle there were loaded 45 parts by weight of the aforementioned mercapto-modified dimethylpolysiloxane "KF-2001", 45 parts by weight of isobutyl methacrylate, 10 parts by weight of methyl methacrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 18

In a 140 mL glass bottle there were loaded 30 parts by weight of the aforementioned mercapto-modified dimethylpolysiloxane "KF-2001", 65 parts by weight of isobutyl methacrylate, 5 parts by weight of methyl methacrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 19

In a 140 mL glass bottle there were loaded 75 parts by weight of the aforementioned mercapto-modified dimethylpolysiloxane "KF-2001", 25 parts by weight of methyl methacrylate, 0.6 part by weight of dimethyl 2,2'-azobis(2-methylpropionate) and 102.4 parts by weight of MEK to a total of 101.5 g, and the procedure was carried out in the same manner as Example 1. The polymerization solution was added dropwise to water while stirring, and the precipitate was recovered and dried at room temperature to obtain a grafted silicone polymer.

Comparative Example 20

In a 225 mL glass bottle there were loaded 67.5 parts by weight of the aforementioned mercapto-modified dimethylpolysiloxane "KF-2001", 23.2 parts by weight of methyl methacrylate, 9.3 parts by weight of methyl acrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Comparative Example 21

In a 140 mL glass bottle there were loaded 67.5 parts by weight of the aforementioned mercapto-modified dimethylpolysiloxane "KF-2001", 12.19 parts by weight of methyl methacrylate, 20.31 parts by weight of methyl acrylate, 0.6 part by weight of dimethyl 2,2'-azobis(2-methylpropionate) and 102.4 parts by weight of MEK to a total of 101.5 g, and the procedure was carried out in the same manner as Example 1. The polymerization solution was added dropwise to water while stirring, and the precipitate was recovered and dried at room temperature to obtain a grafted silicone polymer.

Comparative Example 22

In a 225 mL glass bottle there were loaded 60 parts by weight of the aforementioned mercapto-modified dimethylpolysiloxane "KF-2001", 40 parts by weight of methyl acrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Comparative Example 23

In a 225 mL glass bottle there were loaded 52.5 parts by weight of the aforementioned mercapto-modified dimethylpolysiloxane "KF-2001", 47.5 parts by weight of methyl acrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Comparative Example 24

In a 140 mL glass bottle there were loaded 67.5 parts by weight of the aforementioned mercapto-modified dimethylpolysiloxane "KF-2001", 23.2 parts by weight of methyl methacrylate, 9.3 parts by weight of ethyl acrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 25

In a 140 mL glass bottle there were loaded 60 parts by weight of the aforementioned mercapto-modified dimethylpolysiloxane "KF-2001", 15 parts by weight of methyl methacrylate, 25 parts by weight of ethyl acrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 26

In a 225 mL glass bottle there were loaded 40 parts by weight of the aforementioned mercapto-modified dimethylpolysiloxane "KF-2001", 20 parts by weight of methyl methacrylate, 40 parts by weight of ethyl acrylate, 0.6 part by weight of dimethyl 2,2'-azobis(2-methylpropionate) and 102.4 parts by weight of MEK to a total of 162.4 g, and the procedure was carried out in the same manner as Example 1. The polymerization solution was added dropwise to water while stirring, and the precipitate was recovered and dried at room temperature to obtain a grafted silicone polymer.

Comparative Example 27

In a 225 mL glass bottle there were loaded 60 parts by weight of the aforementioned mercapto-modified dimethylpolysiloxane "KF-2001", 40 parts by weight of ethyl methacrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Comparative Example 28

In a 140 mL glass bottle there were loaded 52.5 parts by weight of the aforementioned mercapto-modified dimethylpolysiloxane "KF-2001", 33.75 parts by weight of ethyl methacrylate, 13.75 parts by weight of methyl acrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 29

In a 140 mL glass bottle there were loaded 52.5 parts by weight of the aforementioned mercapto-modified dimethylpolysiloxane "KF-2001", 33.75 parts by weight of ethyl methacrylate, 13.75 parts by weight of ethyl acrylate, 0.6 part by weight of dimethyl 2,2'-azobis(2-methylpropionate) and 102.4 parts by weight of MEK to a total of 101.5 g, and the procedure was carried out in the same manner as Example 1. The polymerization solution was added dropwise to water while stirring, and the precipitate was recovered and dried at room temperature to obtain a grafted silicone polymer.

Comparative Example 30

In a 140 mL glass bottle there were loaded 40 parts by weight of the aforementioned mercapto-modified dimethylpolysiloxane "KF-2001", 30 parts by weight of ethyl methacrylate, 30 parts by weight of ethyl acrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 31

In a 140 mL glass bottle there were loaded 67.5 parts by weight of the aforementioned mercapto-modified dimethylpolysiloxane "KF-2001", 16.25 parts by weight of methyl methacrylate, 16.25 parts by weight of ethyl methacrylate, 0.6 part by weight of dimethyl 2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 32

In a 140 mL glass bottle there were loaded 80 parts by weight of the aforementioned mercapto-modified dimethylpolysiloxane "KF-2001", 10 parts by weight of isobutyl methacrylate, 10 parts by weight of methacrylic acid, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

Comparative Example 33

In a 225 mL glass bottle there were loaded 60 parts by weight of the aforementioned mercapto-modified dimethylpolysiloxane "KF-2001", 40 parts by weight of isobutyl methacrylate, 0.6 part by weight of 2,2'-azobis(2-methylbutyronitrile) and 100 parts by weight of MEK to a total of 160.48 g, and the procedure was carried out in the same manner as Example 1. The polymerization solution was added dropwise to a methanol:water 2:1 mixed solvent while stirring, and the precipitate was recovered and dried at room temperature to obtain a grafted silicone polymer.

Comparative Example 34

In a 140 mL glass bottle there were loaded 45 parts by weight of the aforementioned mercapto-modified dimethylpolysiloxane "KF-2001", 55 parts by weight of isobutyl methacrylate, 0.6 part by weight of dimethyl 2,2'-azobis(2-methylpropionate) and 102.4 parts by weight of MEK to a total of 81.2 g, and the procedure was carried out in the same manner as Example 1. The polymerization solution was added dropwise to water while stirring, and the precipitate was recovered and dried at room temperature to obtain a grafted silicone polymer.

[Film Properties of Grafted Silicone Polymer: Evaluation of Initial Coated Film]

The grafted silicone polymers obtained in the examples and comparative examples were dissolved in DMCPS to a solid content of 10 weight percent. In cases where the grafted silicone polymer did not dissolve in DMCPS, it was dissolved in MEK to a solid content of 20 weight percent. The polymer solution was coated onto a glass plate using a wire bar to prepare a coated polymer film sample. The film sample was then dried at room temperature for at least 12 hours, and the condition of the dry film was confirmed by hand touch.

Figure 7:
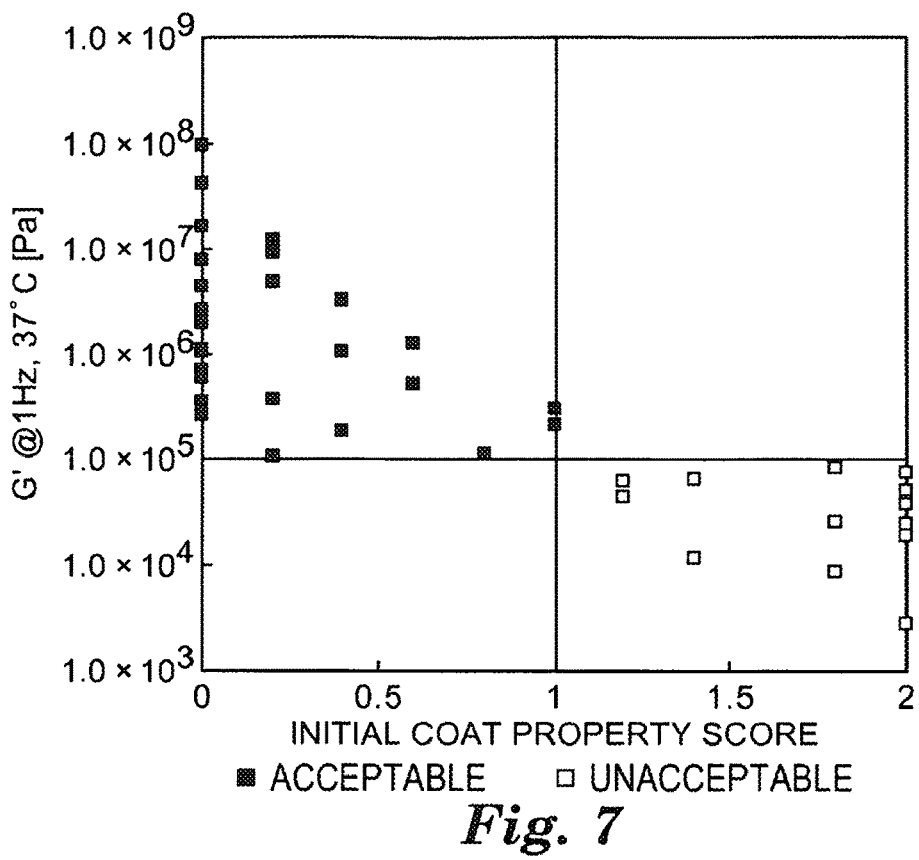
FIG. 7 is a graph plotting elastic storage modulus and initial coat property of the grafted silicone polymer of the invention.

The initial coated film properties were evaluated by a panel of five users who assigned points according to Table 1. A film sample was judged as acceptable if the average of five evaluations based on Table 1 was 1.0 or less. The results are shown in Table 2 and FIG. 7.

Film Properties of Grafted Silicone Polymer: Evaluation of Sebum Resistance.

The grafted silicone polymers obtained in the examples and comparative examples were used to prepare coated polymer film samples in the same manner as was done for evaluation of the initial coated film properties. Each prepared film sample was dried at room temperature for at least 12 hours, and then coated with a suitable amount of macadamia nut oil and allowed to stand for 30 minutes. The macadamia nut oil was used as a sebum substitute. After standing for 30 minutes, the condition of the film was confirmed by hand touch.

Figure 8:
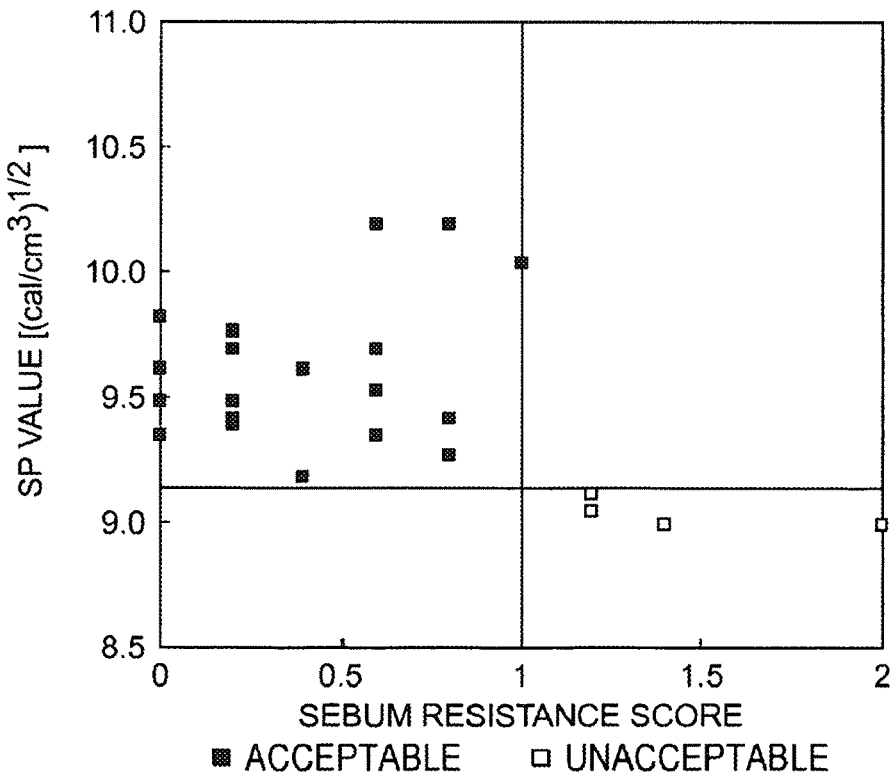
FIG. 8 is a graph plotting SP value and sebum resistance of the grafted silicone polymer of the invention.

The sebum resistance was evaluated by a panel of five users who assigned points according to Table 1. A film sample was judged as acceptable if the average of five evaluations based on Table 1 was 1.0 or less. The results are shown in Table 2 and FIG. 8. (The film samples that had averages of greater than 1.0 in the initial coated film evaluation were not evaluated for sebum resistance.)

TABLE 1

| Points | Initial coat properties | Sebum resistance |
|---|---|---|
| 0 | No stickiness | No stickiness |
| 1 | Slight stickiness but not uncomfortable | Slight stickiness but not uncomfortable |
| 2 | Sticky and uncomfortable | Sticky and uncomfortable |

Viscoelasticity Measurement of Grafted Silicone Polymer.

The viscoelasticities of the grafted silicone polymers obtained in the examples and comparative examples were measured using a 7.9 mm parallel disk-type rotating rheometer ("ARES" by Rheometric Scientific). The measurement results for the elastic storage modulus G' at 37° C., 1 Hz are shown in Table 2 and FIG. 7.

Calculation of Grafted Silicone Polymer Sp Value.

The SP values for the side chains formed by polymerization of the radically polymerizable monomers in the examples and comparative examples were calculated based on the method of Fedors described above. The results are shown in Table 2 and FIG. 8.

Solubility of Grafted Silicone Polymer in DMCPS.

Each of the grafted silicone polymers obtained in the examples and comparative examples was combined with DMCPS to a solid content of 10 weight percent to prepare a polymer solution. After then heating for 2 days at 60° C. with appropriate stirring, the mixture was cooled to 23° C. and the extent of polymer precipitation or solution opacity was visually examined. Mixtures with precipitation or opacity were diluted to 1% solid concentration with DMCPS and examined again. Polymer solutions exhibiting polymer precipitation or solution opacity at 1% solid concentration were judged as unacceptable. That is, the polymer solutions judged as unacceptable mean that the grafted silicone polymers combined with DMCPS did not dissolve in DMCPS in 1 weight percent or greater at 23° C. The results are shown in Table 2.

TABLE 2

| | Initial coat property | | | Sebum resistance | | SP value | DMCPS solubility | |
|---|---|---|---|---|---|---|---|---|
| | Score | Evaluation | G' (Pa) | Score | Evaluation | $(cal/cm^3)^{1/2}$ | Solubility | Evaluation |
| Example 1 | 0.0 | acceptable | $2.5 \times 10^5$ | 0.2 | acceptable | 9.48 | soluble | acceptable |
| Example 2 | 0.0 | acceptable | $3.4 \times 10^5$ | 0 | acceptable | 9.82 | soluble | acceptable |
| Example 3 | 0.8 | acceptable | $1.1 \times 10^5$ | 0.8 | acceptable | 10.19 | soluble | acceptable |
| Example 4 | 0.4 | acceptable | $1.8 \times 10^5$ | 0.2 | acceptable | 9.69 | soluble | acceptable |
| Example 5 | 0.6 | acceptable | $1.3 \times 10^6$ | 0.6 | acceptable | 9.35 | soluble | acceptable |
| Example 6 | 0.0 | acceptable | $7.0 \times 10^5$ | 0.2 | acceptable | 9.77 | soluble | acceptable |
| Example 7 | 1.0 | acceptable | $3.0 \times 10^5$ | 0.4 | acceptable | 9.61 | soluble | acceptable |
| Example 8 | 0.2 | acceptable | $3.6 \times 10^5$ | 0.8 | acceptable | 9.42 | soluble | acceptable |
| Example 9 | 0.6 | acceptable | $5.1 \times 10^5$ | 0.6 | acceptable | 9.52 | soluble | acceptable |
| Example 10 | 0.2 | acceptable | $4.6 \times 10^6$ | 0.8 | acceptable | 9.27 | soluble | acceptable |
| Example 11 | 0.2 | acceptable | $1.1 \times 10^5$ | 0.6 | acceptable | 10.19 | soluble | acceptable |
| Example 12 | 0.0 | acceptable | $5.9 \times 10^5$ | 0.6 | acceptable | 9.69 | soluble | acceptable |
| Example 13 | 1.0 | acceptable | $2.2 \times 10^5$ | 1 | acceptable | 10.04 | soluble | acceptable |
| Comp. Ex. 1 | 0.0 | acceptable | $1.0 \times 10^6$ | 0 | acceptable | 9.48 | insoluble | unacceptable |
| Comp. Ex. 2 | 0.0 | acceptable | $1.1 \times 10^6$ | 0 | acceptable | 9.82 | insoluble | unacceptable |
| Comp. Ex. 3 | 0.0 | acceptable | $3.0 \times 10^5$ | 0 | acceptable | 10.23 | insoluble | unacceptable |
| Comp. Ex. 4 | 0.2 | acceptable | $2.1 \times 10^6$ | 0.2 | acceptable | 9.72 | insoluble | unacceptable |
| Comp. Ex. 5 | 0.0 | acceptable | $4.1 \times 10^7$ | 0 | acceptable | 9.35 | insoluble | unacceptable |
| Comp. Ex. 6 | 0.0 | acceptable | $4.2 \times 10^6$ | 0.2 | acceptable | 9.77 | insoluble | unacceptable |
| Comp. Ex. 7 | 0.0 | acceptable | $6.8 \times 10^5$ | 0 | acceptable | 9.61 | opaque | unacceptable |
| Comp. Ex. 8 | 0.0 | acceptable | $7.5 \times 10^6$ | 0.2 | acceptable | 9.42 | insoluble | unacceptable |
| Comp. Ex. 9 | 0.0 | acceptable | $2.0 \times 10^6$ | 0.2 | acceptable | 9.76 | insoluble | unacceptable |
| Comp. Ex. 10 | 0.2 | acceptable | $1.2 \times 10^7$ | 0.2 | acceptable | 9.39 | insoluble | unacceptable |
| Comp. Ex. 11 | 0.0 | acceptable | $2.5 \times 10^6$ | 0.4 | acceptable | 9.18 | insoluble | unacceptable |
| Comp. Ex. 12 | 0.4 | acceptable | $1.7 \times 10^5$ | 0.6 | acceptable | 10.04 | insoluble | unacceptable |
| Comp. Ex. 13 | 0.0 | acceptable | $2.0 \times 10^5$ | 0 | acceptable | 10.04 | insoluble | unacceptable |
| Comp. Ex. 14 | 0.4 | acceptable | $1.0 \times 10^6$ | 2 | unacceptable | 8.99 | soluble | acceptable |
| Comp. Ex. 15 | 0.2 | acceptable | $9.1 \times 10^6$ | 2 | unacceptable | 8.99 | opaque | unacceptable |
| Comp. Ex. 16 | 0.0 | acceptable | $9.5 \times 10^7$ | 1.4 | unacceptable | 8.99 | insoluble | unacceptable |
| Comp. Ex. 17 | 0.4 | acceptable | $3.1 \times 10^6$ | 1.2 | unacceptable | 9.11 | soluble | acceptable |
| Comp. Ex. 18 | 0.0 | acceptable | $1.6 \times 10^7$ | 1.2 | unacceptable | 9.04 | opaque | unacceptable |
| Comp. Ex. 19 | 1.4 | unacceptable | $1.2 \times 10^4$ | — | — | 9.48 | soluble | acceptable |
| Comp. Ex. 20 | 1.2 | unacceptable | $6.3 \times 10^4$ | — | — | 9.82 | soluble | acceptable |
| Comp. Ex. 21 | 2.0 | unacceptable | $2.8 \times 10^3$ | — | — | 10.19 | soluble | acceptable |
| Comp. Ex. 22 | 2.0 | unacceptable | $3.9 \times 10^4$ | — | — | 10.56 | soluble | acceptable |
| Comp. Ex. 23 | 2.0 | unacceptable | $5.2 \times 10^4$ | — | — | 10.56 | insoluble | unacceptable |
| Comp. Ex. 24 | 1.8 | unacceptable | $8.6 \times 10^3$ | — | — | 9.69 | soluble | acceptable |
| Comp. Ex. 25 | 2.0 | unacceptable | $\leq 1.0 \times 10^5$ | — | — | 9.93 | soluble | acceptable |
| Comp. Ex. 26 | 1.4 | unacceptable | $7.4 \times 10^4$ | — | — | 9.96 | soluble | acceptable |
| Comp. Ex. 27 | 1.4 | unacceptable | $6.4 \times 10^4$ | — | — | 9.35 | soluble | acceptable |
| Comp. Ex. 28 | 2.0 | unacceptable | $7.7 \times 10^4$ | — | — | 9.77 | soluble | acceptable |
| Comp. Ex. 29 | 2.0 | unacceptable | $2.4 \times 10^4$ | — | — | 9.61 | soluble | acceptable |
| Comp. Ex. 30 | 2.0 | unacceptable | $1.9 \times 10^4$ | — | — | 9.80 | soluble | acceptable |
| Comp. Ex. 31 | 1.8 | unacceptable | $2.5 \times 10^4$ | — | — | 9.42 | soluble | acceptable |
| Comp. Ex. 32 | 1.2 | unacceptable | $4.3 \times 10^4$ | — | — | 10.72 | insoluble | unacceptable |
| Comp. Ex. 33 | 2.0 | unacceptable | $\leq 1.0 \times 10^5$ | — | — | 8.99 | soluble | acceptable |
| Comp. Ex. 34 | 1.8 | unacceptable | $8.3 \times 10^4$ | — | — | 8.99 | soluble | acceptable |

Preparation and evaluation of cosmetics containing grafted silicone polymers. Each of the grafted silicone polymers obtained in the examples and comparative examples was used to prepare a cosmetic under the conditions described above, and the cosmetic was evaluated.

Example 14

A W/O-type hand cream was prepared using the grafted silicone polymer of Example 2, as shown in Table 3.

Preparation method: Components (3) and (4) were combined, dissolved at 60° C. and cooled to room temperature, and then components (1) and (2) were added dropwise to prepare an oil-phase component. Separately, components (9) and (10) were mixed while stirring at 60° C., and upon dissolution the mixture was cooled to room temperature and components (5)-(8) were added dropwise to prepare an aqueous-phase component. The aqueous-phase component was then added dropwise to and mixed with the oil-phase component at room temperature to obtain an emulsion. The emulsion was filled into a general-purpose plastic container for use as a W/O-type hand cream.

TABLE 3

| | Component | Parts by wt. |
|---|---|---|
| (1) | Dimethyldistearylammonium hectorite | 0.3 |
| (2) | Polyoxyethylene•methylpolysiloxane copolymer | 1 |
| (3) | DMCPS | 30 |
| (4) | Grafted silicone polymer of Example 2 | 5 |
| (5) | Purified water | 59.45 |
| (6) | Sodium chloride | 0.8 |
| (7) | Tetrasodium hydroxyethanedisulfonate | 0.05 |
| (8) | Phenoxyethanol | 0.2 |
| (9) | 1,3-Butyleneglycol | 3 |
| (10) | Methyl parahydroxybenzoate | 0.2 | he W/O-type hand cream was evaluated by 22 users in terms of the cream spreadability using both hands, the cream feel and any undesirable feel after coating, based on the scale shown in Table 4. The results are shown in Table 5.

TABLE 4

| Points | Cream spreadability | Cream feel | Undesirable feel after coating |
|---|---|---|---|
| 5 | Very good | Moist | Absolutely none |
| 4 | Good | Somewhat moist | None |
| 3 | Average | Neither | Slight |
| 2 | Less than average | Somewhat light | Some |
| 1 | Poor | Light | Significant |

TABLE 5

| User | Gender | Age | Cream spreadability | Cream feel | Undesirable feel after coating |
|---|---|---|---|---|---|
| 1 | female | 40s | 5 | 3 | 5 |
| 2 | female | 30s | 5 | 3 | 5 |
| 3 | female | 30s | 5 | 5 | 2 |
| 4 | female | 40s | 5 | 4 | 5 |
| 5 | female | 30s | 5 | 1 | 5 |
| 6 | female | 30s | 5 | 5 | 3 |
| 7 | male | 20s | 5 | 3 | 5 |
| 8 | female | 40s | 4 | 4 | 4 |
| 9 | female | 50s | 5 | 4 | 4 |
| 10 | female | 30s | 5 | 4 | 3 |
| 11 | female | 40s | 5 | 1 | 5 |
| 12 | female | 50s | 4 | 2 | 4 |
| 13 | female | 20s | 5 | 4 | 5 |
| 14 | female | 10s | 5 | 4 | 5 |
| 15 | female | 20s | 4 | 5 | 5 |
| 16 | female | 20s | 5 | 4 | 4 |
| 17 | female | 20s | 5 | 5 | 4 |
| 18 | female | 20s | 4 | 5 | 5 |
| 19 | female | 20s | 5 | 5 | 5 |
| 20 | female | 20s | 3 | 4 | 3 |
| 21 | female | 20s | 4 | 4 | 5 |
| 22 | female | 20s | 5 | 4 | 4 |
| Average | | | 4.7 | 3.8 | 4.3 |

Since the average for cream spreadability was 4.7, the W/O-type hand creams exhibited highly satisfactory spreading properties and were able to be evenly coated. Also, since the average for the cream quality was 3.8, the W/O-type hand creams had slightly moist feels. When applied, therefore, the creams formed coats with moist feels but no sticky feel and were thus able to maintain smooth feels. Furthermore, since the average for undesirable feeling after coating was 4.3, the W/O-type hand creams formed flexible coats with no undesirable feel.

In order to determine the feel of the creams after washing tableware, samples were applied to both hands of users who were then asked to wash tableware and questioned for their impressions. A lack of stickiness of the applied coat, which prevented adhesion of the hands to tableware and eliminated the need to avoid adhering to clothing, etc., was mentioned as an advantage. In addition, an effect was also observed against roughened skin due to formation of the water-repellent coat.

Example 15

A W/O-type hand cream was prepared in the same manner as Example 14, except that the grafted silicone polymer of Example 1 was used instead of the grafted silicone polymer of Example 2, as shown in Table 6.

TABLE 6

| | Component | Parts by wt. |
|---|---|---|
| (1) | Dimethyldistearylammonium hectorite | 0.3 |
| (2) | Polyoxyethylene•methylpolysiloxane copolymer | 1 |
| (3) | DMCPS | 30 |
| (4) | Grafted silicone polymer of Example 1 | 5 |
| (5) | Purified water | 59.45 |
| (6) | Sodium chloride | 0.8 |
| (7) | Tetrasodium hydroxyethanedisulfonate | 0.05 |
| (8) | Phenoxyethanol | 0.2 |
| (9) | 1,3-Butyleneglycol | 3 |
| (10) | Methyl parahydroxybenzoate | 0.2 |

The W/O-type hand cream was evaluated by five users in terms of cream spreadability using both hands, cream quality and undesirable feeling after coating, based on the scale shown in Table 4. The results are shown in Table 7.

TABLE 7

| User | Gender | Age | Cream spreadability | Cream feel | Undesirable feel after coating |
|---|---|---|---|---|---|
| 1 | female | 40s | 5 | 5 | 5 |
| 2 | female | 30s | 4 | 3 | 5 |
| 3 | female | 40s | 4 | 4 | 4 |
| 4 | female | 30s | 3 | 3 | 4 |
| 5 | female | 30s | 4 | 3 | 4 |
| Average | | | 4 | 3.6 | 4.4 |

Since the average for cream spreadability was 4.0, the W/O-type hand creams exhibited satisfactory spreading properties and were able to be evenly coated. Also, since the average for the cream quality was 3.6, the samples had slightly light feels. Furthermore, since the average for undesirable feeling after coating was 4.4, the W/O-type hand creams formed flexible coats with no undesirable feel.

Example 16

A W/O-type hand cream was prepared in the same manner as Example 14, except that the grafted silicone polymer of Example 5 was used instead of the grafted silicone polymer of Example 2, as shown in Table 8.

TABLE 8

| | Component | Parts by wt. |
|---|---|---|
| (1) | Dimethyldistearylammonium hectorite | 0.3 |
| (2) | Polyoxyethylene•methylpolysiloxane copolymer | 1 |
| (3) | DMCPS | 30 |
| (4) | Grafted silicone polymer of Example 5 | 5 |
| (5) | Purified water | 59.45 |
| (6) | Sodium chloride | 0.8 |
| (7) | Tetrasodium hydroxyethanedisulfonate | 0.05 |
| (8) | Phenoxyethanol | 0.2 |
| (9) | 1,3-Butyleneglycol | 3 |
| (10) | Methyl parahydroxybenzoate | 0.2 |

The cream had satisfactory spreadability when applied to both hands and was able to form an even coat. The cream also formed a flexible coat with no undesirable feel.

Comparative Example 35

A W/O-type hand cream was prepared using the grafted silicone polymer of Comparative Example 15, as shown in Table 9.

Preparation method: Components (4) and (5) were combined at 60° C. and dissolved, and then the mixture was cooed to room temperature. Components (1)-(3) were added dropwise thereto and mixed therewith to prepare an oil-phase component. Separately, components (11) and (12) were mixed while stirring at 60° C., and upon dissolution the mixture was cooled to room temperature and components (6)-(10) were added dropwise to prepare an aqueous-phase component. The aqueous-phase component was then added dropwise to and mixed with the oil-phase component at room temperature to obtain an emulsion. The emulsion was filled into a general-purpose plastic container for use as a W/O-type hand cream.

TABLE 9

| | Component | Parts by wt. |
|---|---|---|
| (1) | Dimethyldistearylammonium hectorite | 0.3 |
| (2) | Polyoxyethylene•methylpolysiloxane copolymer | 1 |
| (3) | Methylphenylpolysiloxane | 0.75 |
| (4) | DMCPS | 15 |
| (5) | Grafted silicone polymer of Comp. Ex. 15 | 2.7 |
| (6) | Purified water | 69.9 |
| (7) | Sodium chloride | 0.8 |
| (8) | Tetrasodium hydroxyethanedisulfonate | 0.05 |
| (9) | Glycerin | 6.1 |
| (10) | Phenoxyethanol | 0.2 |
| (11) | 1,3-Butyleneglycol | 3 |
| (12) | Methyl parahydroxybenzoate | 0.2 |

The obtained W/O-type hand cream exhibited satisfactory spreadability and could be evenly applied, but a noticeable feeling of stickiness after application rendered it unsuitable for use as a hand cream.

Example 17

An O/W-type hand cream was prepared using the grafted silicone polymer of Example 1, as shown in Table 10.

Preparation method: Components (1)-(11) were combined at 75° C. and dissolved. Components (12) and (13) were combined at 60° C. and dissolved, and this polymer solution was cooled to room temperature and then added dropwise and mixed with the earlier mixture to prepare an oil-phase component. Separately, components (14)-(20) were combined and dissolved at 75° C., and then component (21) was added dropwise and mixed therewith to prepare an aqueous-phase component. The oil-phase component and aqueous-phase component were mixed while stirring at 75° C. and then cooled to room temperature to obtain an emulsion. The emulsion was filled into a general-purpose plastic container for use as an O/W-type hand cream.

TABLE 10

| | Component | Parts by wt. |
|---|---|---|
| (1) | Self-emulsifiable glyceryl monostearate | 3 |
| (2) | Sorbitan tristearate | 0.8 |
| (3) | Polyethyleneglycol monostearate | 0.75 |
| (4) | Batyl alcohol | 0.5 |
| (5) | Soybean phospholipid | 0.05 |
| (6) | Glycerin tri(caprylate/caprate) | 6 |
| (7) | Vegetable squalane | 5 |
| (8) | Natural vitamin E | 0.05 |
| (9) | Stearic acid | 1 |
| (10) | Propyl parahydroxybenzoate | 0.1 |
| (11) | Polyoxyethylene/methylpolysiloxane copolymer | 1.5 |
| (12) | DMCPS | 8 |
| (13) | Grafted silicone polymer of Example 1 | 2 |
| (14) | Dipropylene glycol | 5 |
| (15) | Methyl parahydroxybenzoate | 0.2 |

TABLE 10-continued

| | Component | Parts by wt. |
|---|---|---|
| (16) | Purified water | 59.14 |
| (17) | Tetrasodium hydroxyethanedisulfonate | 0.08 |
| (18) | Concentrated glycerin | 1 |
| (19) | Potassium hydroxide | 0.03 |
| (20) | Sucrose fatty acid ester | 0.8 |
| (21) | 2% Carboxyvinyl polymer aqueous solution | 5 |

The O/W-type hand cream had satisfactory spreadability when applied to both hands, and a light feel. The O/W-type hand cream also formed a flexible coat with no undesirable feel.

Example 18

A W/O-type sunscreen lotion was prepared using the grafted silicone polymer of Example 2, as shown in Table 11.

Preparation method: Components (10) and (11) were combined at 60° C. and dissolved, and then the mixture was cooled to room temperature. Components (1)-(9) and (12)-(14) were then added dropwise thereto and mixed therewith to prepare an oil-phase component. Separately, components (16) and (17) were mixed to dissolution while stirring at 60° C., and after cooling to room temperature, component (15) was added dropwise and mixed therewith to prepare an aqueous-phase component. The aqueous-phase component was added dropwise to and mixed with the oil-phase component to obtain an emulsion. The emulsion was filled into a general-purpose plastic container for use as a W/O-type sunscreen lotion.

TABLE 11

| | Component | Parts by wt. |
|---|---|---|
| (1) | Zinc oxide | 13.5 |
| (2) | Stearic acid-treated titanium dioxide fine particles | 8.5 |
| (3) | Methyl parahydroxybenzoate | 0.1 |
| (4) | Polyglyceryl diisostearate | 1.3 |
| (5) | dl-α-Tocopherol acetate | 0.05 |
| (6) | Polyoxyethylene•methylpolysiloxane copolymer | 7.3 |
| (7) | Polyglyceryl monoisostearate | 0.2 |
| (8) | Polyglyceryl diisostearate | 1.5 |
| (9) | Neopentylglycol dicaprate | 5 |
| (10) | Grafted silicone polymer of Example 2 | 5.85 |
| (11) | DMCPS | 28.05 |
| (12) | Methylpolysiloxane | 0.75 |
| (13) | Phenoxyethanol | 0.5 |
| (14) | Nylon powder | 4 |
| (15) | Purified water | 19.3 |
| (16) | Methyl parahydroxybenzoate | 0.1 |
| (17) | 1,3-Butyleneglycol | 4 |

The W/O-type sunscreen lotion had satisfactory spreadability when applied to both hands, and a light feel. The W/O-type sunscreen lotion also could be uniformly and evenly applied, and formed a flexible coat with no undesirable feel.

Example 19

A mascara was prepared using the grafted silicone polymer of Example 1, as shown in Table 12.

Preparation method: Components (12) and (13) were combined and dissolved at 60° C., and then the solution was cooled to room temperature and components (14) and (15) were added dropwise to prepare a polymer solution. Separately, components (1)-(11) were combined at 90° C. and dissolved to prepare a solution. The polymer solution was added dropwise to this solution at 90° C., and after mixing the solutions, the resulting mixture was thoroughly stirred while cooling to room temperature to obtain an oily paste. The oily paste was filled into a mascara container for use as mascara.

TABLE 12

| | Component | Parts by wt. |
|---|---|---|
| (1) | Propyl parahydroxybenzoate | 0.2 |
| (2) | Candelilla resin | 1.8 |
| (3) | Paraffin | 17.25 |
| (4) | Microcrystalline wax | 10.7 |
| (5) | White beeswax | 1 |
| (6) | Polyethylene wax | 3.1 |
| (7) | Natural vitamin E | 0.1 |
| (8) | Dextrin palmitate | 1 |
| (9) | Light liquid isoparaffin | 29.2 |
| (10) | Dimethyldistearylammonium hectorite | 2 |
| (11) | Ethanol | 1 |
| (12) | Grafted silicone polymer of Example 1 | 5 |
| (13) | DMCPS | 20 |
| (14) | Light liquid paraffin | 2.65 |
| (15) | Black iron oxide | 5 |

The mascara was evaluated by a panel of five users in terms of voluminous feel when applied onto the eyelashes, long-lasting function of the mascara and curl retention, based on the scale shown in Table 13. The results are shown in Table 14.

TABLE 13

| Points | Voluminous feel | Long-lasting function | Curl retention |
|---|---|---|---|
| 5 | Very good | Very good. Resistant to smudge | Very excellent |
| 4 | Good | Good | Excellent |
| 3 | Average | Average | Average |
| 2 | Poor | Poor | Poor |
| 1 | Very poor | Very poor. Prone to smudge | Very poor |

TABLE 14

| User | Gender | Age | Voluminous feel | Long-lasting function | Curl retention |
|---|---|---|---|---|---|
| 1 | female | 40s | 5 | 5 | 5 |
| 2 | female | 30s | 3 | 4 | 4 |
| 3 | female | 40s | 3 | 4 | 4 |
| 4 | female | 30s | 4 | 4 | 3 |
| 5 | female | 30s | 3 | 3 | 3 |
| | Average | | 3.6 | 4 | 3.8 |

Since the average for the voluminous feel of the mascara was 3.6, it was judged that the mascara produces a feeling of volume on the eyelashes. Also, since the average for the long-lasting function of the mascara was 4.0, the mascara was shown to be able to prevent makeup deterioration due to sweat, tears and sebum. The average for curl retention by the mascara was 3.8, thus suggesting excellent ability to maintain eyelash curl.

Example 20

A W/O-type liquid foundation was prepared using the grafted silicone polymer of Example 1, as shown in Table 15.
Preparation method: Components (13) and (14) were combined and dissolved at 60° C. and cooled to room temperature, and then components (1)-(12) and (15)-(17) were added dropwise and mixed therewith to prepare an oil-phase component. Separately, components (18) and (20)-(23) were mixed while stirring to dissolution at ordinary temperature, and then component (19) was added dropwise and mixed therewith to prepare an aqueous-phase component. The aqueous-phase component was then added dropwise to and mixed with the oil-phase component at room temperature to obtain an emulsion. The emulsion was filled into a bottle container for use as a W/O-type liquid foundation.

TABLE 15

| | Component | Parts by wt. |
|---|---|---|
| (1) | Natural vitamin E | 0.5 |
| (2) | Glyceryl tri-2-ethylhexanoate | 8.8 |
| (3) | Methylpolysiloxane | 1.5 |
| (4) | Myristic acid-treated titanium dioxide | 6 |
| (5) | Myristic acid-treated red iron oxide | 0.6 |
| (6) | Myristic acid-treated yellow iron oxide | 2.12 |
| (7) | Myristic acid-treated black iron oxide | 0.28 |
| (8) | Phenoxyethanol | 0.5 |
| (9) | Sorbitan sesquiisostearate | 1.5 |
| (10) | Sorbitan sesquioleate | 0.5 |
| (11) | Alkyl polyacrylate | 3 |
| (12) | DMCPS | 8 |
| (13) | Grafted silicone polymer of Example 1 | 2.5 |
| (14) | Zinc oxide | 7 |
| (15) | Stearic acid-treated titanium dioxide fine particles | 4.7 |
| (16) | Polyoxyethylene•methylpolysiloxane copolymer | 8.5 |
| (17) | Purified water | 37 |
| (18) | Magnesium aluminum silicate | 0.5 |
| (19) | Sodium chloride | 1 |
| (20) | Sodium citrate | 0.5 |
| (21) | 1,2-Pentanediol | 3 |
| (22) | 1,3-Butyleneglycol | 2 |

The W/O-type liquid foundation was evaluated by a panel of five users in terms of foundation spreadability and long-lasting function of the liquid foundation, based on the scale shown in Table 16. The results are shown in Table 17.

TABLE 16

| Points | Foundation spreadability | Long-lasting function of foundation |
|---|---|---|
| 5 | Very good | Very good |
| 4 | Good | Good |
| 3 | Average | Average |
| 2 | Poor | Poor |
| 1 | Very poor | Very poor |

TABLE 17

| User | Gender | Age | Foundation spreadability | Long-lasting function of foundation |
|---|---|---|---|---|
| 1 | Female | 40s | 4 | 5 |
| 2 | Female | 30s | 3 | 3 |
| 3 | Female | 40s | 4 | 4 |
| 4 | Female | 30s | 4 | 4 |
| 5 | Female | 30s | 3 | 3 |
| | Average | | 3.6 | 3.8 |

Since the average for the spreadability of the W/O-type liquid foundation was 3.6, it exhibited satisfactory spreadability and was able to be evenly applied. Also, since the average for the long-lasting function of the foundation was 3.8, it was shown to be able to prevent makeup deterioration due to sweat, tears and sebum.

This invention provides a grafted silicone polymer which has sufficiently high solubility in non-skin-irritating volatile solvents to thus ensure sufficient freedom of formulation, and which when used as a cosmetic component is able to form coatings with a minimal sticky feel on the skin and satisfactory water and sebum resistance, and cosmetics that contain the grafted silicone polymer.

What is claimed is:

1. A grafted silicone polymer comprising a polymerization product of
   (a) a mercapto-modified silicone polymer represented by general formula (2)

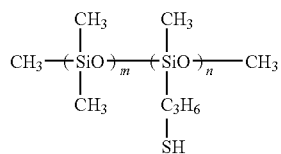

where m represents an integer of 10-540 and n represents an integer of 1 or greater, and
   (b) a radically polymerizable monomer component comprising (meth)acrylic acid and/or a (meth)acrylic acid alkyl ester, selected so that the solubility parameter of a polymer obtained only from the radically polymerizable monomer component is at least 9.14 $(cal/cm^3)^{1/2}$,
wherein the grafted silicone polymer has a elastic storage modulus of $1 \times 10^5$ Pa or greater at 37° C., 1 Hz and dissolves in decamethylcyclopentasiloxane (DMCPS) in an amount of 1 weight percent or greater at 23° C., and
wherein said graft silicone polymer is obtained by polymerizing a mercapto-modified silicone polymer (MMSP) represented by general formula (2), methyl methacrylate (MMA) and methyl acrylate (MA), and has a composition in the range defined by
(MMSP)/(MMA)/(MA)=63.7/36.3/0.0
(MMSP)/(MMA)/(MA)=46.2/26.9/26.9
(MMSP)/(MMA)/(MA)=46.2/7.6/46.2
(MMSP)/(MMA)/(MA)=63.7/7.6/28.7
(MMSP)/(MMA)/(MA)=63.7/25.9/10.4
(MMSP)/(MMA)/(MA)=71.2/29.8/0.0
in the ternary phase diagram shown in FIG. 1.

2. A grafted silicone polymer comprising a polymerization product of
   (a) a mercapto-modified silicone polymer represented by general formula (2)

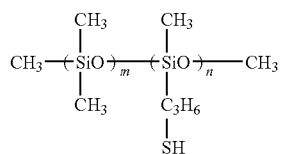

where m represents an integer of 10-540 and n represents an integer of 1 or greater, and
   (b) a radically polymerizable monomer component comprising (meth)acrylic acid and/or a (meth)acrylic acid alkyl ester, selected so that the solubility parameter of a polymer obtained only from the radically polymerizable monomer component is at least 9.14 $(cal/cm^3)^{1/2}$,
wherein the grafted silicone polymer has a elastic storage modulus of $1 \times 10^5$ Pa or greater at 37° C., 1 Hz and dissolves in decamethylcyclopentasiloxane (DMCPS) in an amount of 1 weight percent or greater at 23° C., and
wherein said grafted silicone polymer is obtained by polymerizing a mercapto-modified silicone polymer (MMSP) represented by general formula (2), methyl methacrylate (MMA) and ethyl acrylate (EA), and has a composition in the range defined by
(MMSP)/(MMA)/(EA)=63.7/36.3/0.0
(MMSP)/(MMA)/(EA)=46.2/36.3/17.5
(MMSP)/(MMA)/(EA)=46.2/21.8/32.0
(MMSP)/(MMA)/(EA)=63.7/21.8/14.5
(MMSP)/(MMA)/(EA)=63.7/25.9/10.4
(MMSP)/(MMA)/(EA)=71.2/29.8/0.0
in the ternary phase diagram shown in FIG. 2.

3. A grafted silicone polymer comprising a polymerization product of
   (a) a mercapto-modified silicone polymer represented by general formula (2,)

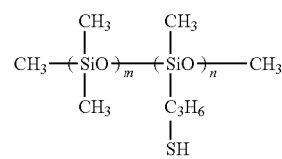

where m represents an integer of 10-540 and n represents an integer of 1 or greater, and
   (b) a radically polymerizable monomer component comprising (meth)acrylic acid and/or
   a (meth)acrylic acid alkyl ester, selected so that the solubility parameter of a polymer obtained only from the radically polymerizable monomer component is at least 9.14 $(cal/cm^3)^{1/2}$,
wherein the grafted silicone polymer has a elastic storage modulus of $1 \times 10^5$ Pa or greater at 37° C., 1 Hz and dissolves in decamethylcyclopentasiloxane (DMCPS) in an amount of 1 weight percent or greater at 23° C., and
wherein said grafted silicone polymer is obtained by polymerizing a mercapto-modified silicone polymer (MMSP) represented by general formula (2), ethyl methacrylate (EMA) and methyl acrylate (MA), and has a composition in the range defined by
(MMSP)/(EMA)/(MA)=46.2/53.8/0.0
(MMSP)/(EMA)/(MA)=35.0/53.8/11.2
(MMSP)/(EMA)/(MA)=30.0/35.0/35.0
(MMSP)/(EMA)/(MA)=46.2/18.8/35.0
(MMSP)/(EMA)/(MA)=46.2/38.4/15.4
(MMSP)/(EMA)/(MA)=56.3/43.7/0.0
in the ternary phase diagram shown in FIG. 3.

4. A grafted silicone polymer comprising a polymerization product of
   (a) a mercapto-modified silicone polymer represented by general formula (2)

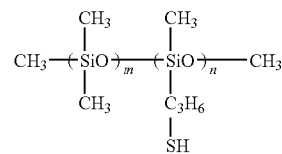

where m represents an integer of 10-540 and n represents an integer of 1 or greater, and (b) a radically polymerizable monomer component comprising (meth)acrylic acid and/or a (meth)acrylic acid alkyl ester, selected so that the solubility parameter of a polymer obtained only from the radically polymerizable monomer component is at least 9.14 $(cal/cm^3)^2$, wherein the grafted silicone polymer has a elastic storage modulus of $1\times10^5$ Pa or greater at 37° C., 1 Hz and dissolves in decamethylcyclopentasiloxane (DMCPS) in an amount of 1 weight percent or greater at 23° C., and wherein said grafted silicone polymer is obtained by polymerizing a mercapto-modified silicone polymer (MMSP) represented by general formula (2), isobutyl methacrylate (IBMA) and methacrylic acid (MAA), and has a composition in the range defined by (MMSP)/(IBMA)/(MAA)=70.0/22.5/7.5
(MMSP)/(IBMA)/(MAA)=42.5/52.9/4.6
(MMSP)/(IBMA)/(MAA)=42.5/55.7/1.8
(MMSP)/(IBMA)/(MAA)=70.0/29.0/1.0 in the ternary phase diagram shown in FIG. 6.

5. A cosmetic containing a grafted silicone polymer according to claim 1.

6. A cosmetic containing a grafted silicone polymer according to claim 2.

7. A cosmetic containing a grafted silicone polymer according to claim 3.

8. A cosmetic containing a grafted silicone polymer according to claim 4.

* * * * *

UNITED STATES PATENT AND TRADEMARK OFFICE
CERTIFICATE OF CORRECTION

PATENT NO. : 8,258,243 B2
APPLICATION NO. : 12/596859
DATED : September 4, 2012
INVENTOR(S) : Takeshi Yamada It is certified that error appears in the above-identified patent and that said Letters Patent is hereby corrected as shown below:

Column 2
Line 8, Delete " 1 Œ 105 " and insert -- $1 \times 10^5$ --, therefor.

Column 4
Line 64, Delete "ally," and insert -- allyl, --, therefor.

Column 6
Lines 20-21, Delete "-cyanopentanonoic" and insert -- -cyanopentanoic --, therefor.
Line 31, Delete "acylphosphone" and insert -- acylphosphine --, therefor.

Column 9
Line 31, Delete "2-decyltetradecinol," and insert -- 2-decyltetradecanol, --, therefor.

Column 21
Line 10, Delete "2'-azobis" and insert -- 2,2'-azobis --, therefor.

Column 22
Line 45, Delete "Sp" and insert -- SP --, therefor.

Column 24
Line 64, Delete "he" and insert -- The --, therefor.

Column 32
Line 17, In Claim 3, delete "(2,)" and insert -- (2) --, therefor.

Column 33
Line 5, In Claim 4, delete "$(cal/cm^3)^2$," and insert -- $(cal/cm^3)^{1/2}$, --, therefor.
Line 9, In Claim 4, delete "1weight" and insert -- 1 weight --, therefor.

Signed and Sealed this
Fifteenth Day of January, 2013

David J. Kappos
*Director of the United States Patent and Trademark Office*